(12) United States Patent
Malaviya et al.

(10) Patent No.: US 7,569,233 B2
(45) Date of Patent: Aug. 4, 2009

(54) HYBRID BIOLOGIC-SYNTHETIC BIOABSORBABLE SCAFFOLDS

(75) Inventors: Prasanna Malaviya, Fort Wayne, IN (US); Janine M. Orban, Warsaw, IN (US); Philip J. Jenks, Warsaw, IN (US); Terrence D. Whalen, Leesburg, IN (US)

(73) Assignee: DePuy Products, Inc., Warsaw, IN (US)

( * ) Notice: Subject to any disclaimer, the term of this patent is extended or adjusted under 35 U.S.C. 154(b) by 201 days.

(21) Appl. No.: 11/110,169

(22) Filed: Apr. 20, 2005

(65) Prior Publication Data

US 2005/0249771 A1 Nov. 10, 2005

Related U.S. Application Data

(60) Provisional application No. 60/567,886, filed on May 4, 2004, provisional application No. 60/571,766, filed on May 17, 2004.

(51) Int. Cl.
*B27N 3/00* (2006.01)
*A61F 2/00* (2006.01)
*A61F 2/02* (2006.01)
*C12N 9/10* (2006.01)

(52) U.S. Cl. ......................... 424/422; 424/423; 264/109
(58) Field of Classification Search ........................ None
See application file for complete search history.

(56) References Cited

U.S. PATENT DOCUMENTS

| | | | |
|---|---|---|---|
| 3,272,204 A | 9/1966 | Artandi et al. |
| 3,562,820 A | 2/1971 | Braun |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,352,463 A | 10/1982 | Baker |
| 4,400,833 A | 8/1983 | Kurland |
| 4,418,691 A | 12/1983 | Yannas et al. |
| 4,610,397 A | 9/1986 | Fischer et al. |
| 4,642,120 A | 2/1987 | Nevo et al. |
| 4,669,473 A | 6/1987 | Richards et al. |
| 4,703,108 A | 10/1987 | Silver et al. |
| 4,705,040 A | 11/1987 | Mueller et al. |
| 4,741,330 A | 5/1988 | Hayhurst |
| 4,750,492 A | 6/1988 | Jacobs |
| 4,846,835 A | 7/1989 | Grande |
| 4,873,976 A | 10/1989 | Schreiber |
| 4,880,429 A | 11/1989 | Stone |
| 4,902,508 A | 2/1990 | Badylak et al. |
| 4,919,667 A | 4/1990 | Richmond |
| 4,956,178 A | 9/1990 | Badylak et al. |
| 4,956,179 A | 9/1990 | Bamberg et al. |
| 4,976,715 A | 12/1990 | Bays et al. |
| 5,007,934 A | 4/1991 | Stone |
| 5,061,286 A | 10/1991 | Lyle |
| 5,102,421 A | 4/1992 | Anspach, Jr. |
| 5,108,438 A | 4/1992 | Stone |
| 5,128,326 A | 7/1992 | Balazs et al. |
| RE34,021 E | 8/1992 | Mueller et al. |
| 5,236,431 A | 8/1993 | Gogolewski et al. |
| 5,246,441 A | 9/1993 | Ross et al. |
| 5,258,015 A | 11/1993 | Li et al. |
| 5,269,809 A | 12/1993 | Hayhurst et al. |
| 5,275,826 A | 1/1994 | Badylak et al. |
| 5,281,422 A | 1/1994 | Badylak et al. |
| 5,306,311 A | 4/1994 | Stone et al. |
| 5,320,633 A | 6/1994 | Allen et al. |
| 5,329,846 A | 7/1994 | Bonutti |
| 5,350,583 A | 9/1994 | Yoshizato et al. |
| 5,352,463 A | 10/1994 | Badylak et al. |
| 5,372,821 A | 12/1994 | Badylak et al. |
| 5,374,268 A | 12/1994 | Sander |
| 5,376,118 A | 12/1994 | Kaplan et al. |
| 5,380,334 A | 1/1995 | Torrier et al. |
| 5,445,833 A | 8/1995 | Badylak et al. |
| 5,447,940 A | 9/1995 | Harvey et al. |
| 5,460,962 A | 10/1995 | Kemp |
| 5,464,929 A | 11/1995 | Bezwada et al. |
| 5,479,033 A | 12/1995 | Baca et al. |
| 5,514,181 A | 5/1996 | Light et al. |

(Continued)

FOREIGN PATENT DOCUMENTS

EP 0 446 105 A2 1/1992

(Continued)

OTHER PUBLICATIONS

Hiles et al., "Mechanical properties of xenogeneic small-intestinal submucosa when used as an aortic graft in the dog", *Journal of Biomedical Materials Research*, vol. 29, 883-891, (1995).

(Continued)

*Primary Examiner*—Jon P Weber
*Assistant Examiner*—Kailash C Srivastava
(74) *Attorney, Agent, or Firm*—Barnes & Thornburg LLP

(57) ABSTRACT

A bioprosthetic device is provided for soft tissue attachment, reinforcement, and or reconstruction. The device comprises a naturally occurring extracellular matrix portion and a synthetic portion.

25 Claims, 5 Drawing Sheets

U.S. PATENT DOCUMENTS

| | | | |
|---|---|---|---|
| 5,516,533 A | 5/1996 | Badylak et al. |
| 5,520,691 A | 5/1996 | Branch |
| 5,545,178 A | 8/1996 | Kensey et al. |
| 5,554,389 A | 9/1996 | Badylak et al. |
| 5,569,252 A | 10/1996 | Justin et al. |
| 5,573,784 A | 11/1996 | Badylak et al. |
| 5,591,234 A | 1/1997 | Kirsch |
| 5,593,441 A | 1/1997 | Lichtenstein et al. |
| 5,595,621 A | 1/1997 | Light et al. |
| 5,595,751 A | 1/1997 | Bezwada et al. |
| 5,597,579 A | 1/1997 | Bezwada et al. |
| 5,601,558 A | 2/1997 | Torrie et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,626,614 A | 5/1997 | Hart |
| 5,630,824 A | 5/1997 | Hart |
| 5,632,745 A | 5/1997 | Schwartz |
| 5,641,518 A | 6/1997 | Badylak et al. |
| 5,645,850 A | 7/1997 | Bezwada et al. |
| 5,645,860 A | 7/1997 | Knapp, Jr. et al. |
| 5,648,088 A | 7/1997 | Bezwada et al. |
| 5,660,225 A | 8/1997 | Saffran |
| 5,668,288 A | 9/1997 | Storey et al. |
| 5,669,912 A | 9/1997 | Spetzler |
| 5,677,355 A | 10/1997 | Shalaby et al. |
| 5,681,353 A | 10/1997 | Li et al. |
| 5,693,085 A | 12/1997 | Buirge et al. |
| 5,695,998 A | 12/1997 | Badylak et al. |
| 5,698,213 A | 12/1997 | Jamiolkowski et al. |
| 5,700,583 A | 12/1997 | Jamiolkowski et al. |
| 5,702,462 A | 12/1997 | Oberlander |
| 5,711,960 A | 1/1998 | Shikinami |
| 5,711,969 A | 1/1998 | Patel et al. |
| 5,725,556 A | 3/1998 | Moser et al. |
| 5,730,933 A | 3/1998 | Peterson |
| 5,733,337 A | 3/1998 | Carr, Jr. et al. |
| 5,733,868 A | 3/1998 | Peterson et al. |
| 5,735,897 A | 4/1998 | Buirge |
| 5,735,903 A | 4/1998 | Li et al. |
| 5,736,372 A | 4/1998 | Vacanti et al. |
| 5,753,267 A | 5/1998 | Badylak et al. |
| 5,755,791 A | 5/1998 | Whitson et al. |
| 5,759,190 A | 6/1998 | Vibe-Hansen et al. |
| 5,759,205 A | 6/1998 | Valentini |
| 5,762,600 A | 6/1998 | Bruchman et al. |
| 5,762,966 A | 6/1998 | Knapp et al. |
| 5,769,899 A | 6/1998 | Schwartz et al. |
| 5,773,577 A | 6/1998 | Cappello |
| 5,788,625 A | 8/1998 | Plouhar et al. |
| 5,795,353 A | 8/1998 | Felt |
| 5,800,537 A | 9/1998 | Bell |
| 5,830,708 A | 11/1998 | Naughton |
| 5,834,232 A | 11/1998 | Bishop et al. |
| 5,842,477 A | 12/1998 | Naughton et al. |
| 5,847,012 A | 12/1998 | Shalaby et al. |
| 5,855,610 A | 1/1999 | Vacanti et al. |
| 5,855,613 A | 1/1999 | Antanavich et al. |
| 5,855,619 A | 1/1999 | Caplan et al. |
| 5,859,150 A | 1/1999 | Jamiolkowski et al. |
| 5,861,004 A | 1/1999 | Kensey et al. |
| 5,863,551 A | 1/1999 | Woerly |
| 5,866,414 A | 2/1999 | Badylak et al. |
| 5,885,619 A | 3/1999 | Patel et al. |
| 5,891,558 A | 4/1999 | Bell et al. |
| 5,899,939 A | 5/1999 | Boyce et al. |
| 5,906,997 A | 5/1999 | Schwartz et al. |
| 5,916,265 A | 6/1999 | Hu |
| 5,922,028 A | 7/1999 | Plouhar et al. |
| 5,939,323 A | 8/1999 | Valentini et al. |
| 5,954,723 A | 9/1999 | Spetzler |
| 5,954,747 A | 9/1999 | Clark |
| 5,955,100 A | 9/1999 | Bosslet et al. |
| 5,958,874 A | 9/1999 | Clark et al. |
| 5,968,096 A | 10/1999 | Whitson et al. |
| 5,971,987 A | 10/1999 | Huxel et al. |
| 5,980,524 A | 11/1999 | Justin et al. |
| 5,981,802 A | 11/1999 | Katz |
| 5,981,825 A | 11/1999 | Brekke |
| 5,989,269 A | 11/1999 | Vibe-Hansen et al. |
| 5,989,280 A | 11/1999 | Euteneuer et al. |
| 5,993,475 A | 11/1999 | Lin et al. |
| 5,993,844 A | 11/1999 | Abraham et al. |
| 5,997,575 A | 12/1999 | Whitson et al. |
| 6,010,525 A | 1/2000 | Bonutti et al. |
| 6,017,301 A | 1/2000 | Schwartz et al. |
| 6,017,348 A | 1/2000 | Hart et al. |
| 6,027,744 A | 2/2000 | Vacanti et al. |
| 6,034,140 A | 3/2000 | Schwartz et al. |
| 6,042,610 A | 3/2000 | Li et al. |
| 6,051,750 A | 4/2000 | Bell |
| 6,056,752 A | 5/2000 | Roger |
| 6,056,777 A | 5/2000 | McDowell |
| 6,056,778 A | 5/2000 | Grafton et al. |
| 6,060,640 A | 5/2000 | Pauley et al. |
| 6,066,160 A | 5/2000 | Colvin et al. |
| 6,068,648 A | 5/2000 | Cole et al. |
| 6,077,989 A | 6/2000 | Kandel et al. |
| 6,080,194 A | 6/2000 | Pachence et al. |
| 6,093,201 A | 7/2000 | Cooper et al. |
| 6,098,347 A | 8/2000 | Jaeger et al. |
| 6,099,567 A | 8/2000 | Badylak et al. |
| 6,110,212 A | 8/2000 | Gregory |
| 6,117,979 A * | 9/2000 | Hendriks et al. ............ 530/356 |
| 6,126,686 A | 10/2000 | Badylak et al. |
| 6,133,325 A | 10/2000 | Schwartz et al. |
| 6,146,385 A | 11/2000 | Torrie et al. |
| 6,152,935 A | 11/2000 | Kammerer et al. |
| 6,153,292 A | 11/2000 | Bell et al. |
| 6,156,044 A | 12/2000 | Kammerer et al. |
| 6,165,225 A | 12/2000 | Antanavich et al. |
| 6,166,184 A * | 12/2000 | Hendriks et al. ............ 530/356 |
| 6,171,344 B1 | 1/2001 | Atala |
| 6,176,880 B1 | 1/2001 | Plouhar et al. |
| 6,179,840 B1 | 1/2001 | Bowman |
| 6,179,872 B1 | 1/2001 | Bell et al. |
| 6,187,039 B1 | 2/2001 | Hiles et al. |
| 6,197,296 B1 | 3/2001 | Davies et al. |
| 6,206,931 B1 | 3/2001 | Cook et al. |
| 6,214,048 B1 | 4/2001 | Ito et al. |
| 6,214,049 B1 | 4/2001 | Gayer et al. |
| 6,224,892 B1 | 5/2001 | Searle |
| 6,235,057 B1 | 5/2001 | Roger et al. |
| 6,242,247 B1 | 6/2001 | Rieser et al. |
| 6,251,143 B1 | 6/2001 | Schwartz et al. |
| 6,251,876 B1 | 6/2001 | Bellini et al. |
| 6,258,124 B1 | 7/2001 | Darois et al. |
| 6,264,702 B1 | 7/2001 | Ory et al. |
| 6,265,333 B1 | 7/2001 | Dzenis et al. |
| 6,267,957 B1 | 7/2001 | Green et al. |
| 6,270,530 B1 | 8/2001 | Eldridge et al. |
| 6,273,893 B1 | 8/2001 | McAllen, III et al. |
| 6,280,473 B1 | 8/2001 | Lemperle et al. |
| 6,280,474 B1 | 8/2001 | Cassidy et al. |
| 6,283,980 B1 | 9/2001 | Vibe-Hansen et al. |
| 6,288,043 B1 | 9/2001 | Spiro et al. |
| 6,290,711 B1 | 9/2001 | Caspari et al. |
| 6,293,961 B2 | 9/2001 | Schwartz et al. |
| 6,294,041 B1 | 9/2001 | Boyce et al. |
| 6,299,905 B1 | 10/2001 | Peterson et al. |
| 6,306,156 B1 | 10/2001 | Clark |
| 6,306,159 B1 | 10/2001 | Schwartz et al. |
| 6,306,177 B1 | 10/2001 | Felt et al. |
| 6,319,258 B1 | 11/2001 | McAllen, III et al. |

| | | | |
|---|---|---|---|
| 6,319,271 B1 | 11/2001 | Schwartz et al. | |
| 6,326,025 B1 | 12/2001 | Sigler et al. | |
| 6,333,029 B1 | 12/2001 | Vyakarnam et al. | |
| 6,334,872 B1 | 1/2002 | Termin et al. | |
| 6,355,699 B1 | 3/2002 | Vyakarnam et al. | |
| 6,358,284 B1 | 3/2002 | Fearnot et al. | |
| 6,364,884 B1 | 4/2002 | Bowman et al. | |
| 6,371,958 B1 | 4/2002 | Overaker | |
| 6,373,221 B1 | 4/2002 | Koike et al. | |
| 6,379,367 B1 | 4/2002 | Vibe-Hansen et al. | |
| 6,379,710 B1 | 4/2002 | Badylak | |
| 6,383,221 B1 | 5/2002 | Scarborough et al. | |
| 6,387,693 B2 | 5/2002 | Rieser et al. | |
| 6,402,766 B2 | 6/2002 | Bowman et al. | |
| 6,409,764 B1 | 6/2002 | White et al. | |
| 6,423,073 B2 | 7/2002 | Bowman | |
| 6,436,110 B2 | 8/2002 | Bowman et al. | |
| 6,440,444 B2 | 8/2002 | Boyce et al. | |
| 6,447,517 B1 | 9/2002 | Bowman | |
| 6,451,032 B1 | 9/2002 | Ory et al. | |
| 6,458,158 B1 | 10/2002 | Anderson et al. | |
| 6,458,383 B2 | 10/2002 | Chen et al. | |
| 6,464,729 B1 | 10/2002 | Kandel | |
| 6,497,650 B1 | 12/2002 | Nicolo | |
| 6,497,707 B1 | 12/2002 | Bowman et al. | |
| 6,508,821 B1 | 1/2003 | Schwartz et al. | |
| 6,517,564 B1 | 2/2003 | Grafton et al. | |
| 6,566,345 B2 | 5/2003 | Miller et al. | |
| 6,572,650 B1 | 6/2003 | Abraham et al. | |
| 6,592,623 B1 | 7/2003 | Bowlin et al. | |
| 6,638,312 B2 * | 10/2003 | Plouhar et al. | 623/23.72 |
| 6,652,872 B2 | 11/2003 | Nevo et al. | |
| 6,666,892 B2 | 12/2003 | Hiles et al. | |
| 6,692,499 B2 | 2/2004 | Törmälä et al. | |
| 6,812,221 B2 | 11/2004 | McKeehan et al. | |
| 6,840,962 B1 | 1/2005 | Vacanti et al. | |
| 6,869,938 B1 | 3/2005 | Schwartz et al. | |
| 6,989,034 B2 | 1/2006 | Hammer et al. | |
| 2001/0002446 A1 | 5/2001 | Plouhar et al. | |
| 2001/0023373 A1 | 9/2001 | Plouhar et al. | |
| 2001/0024658 A1 | 9/2001 | Chen et al. | |
| 2001/0043943 A1 | 11/2001 | Coffey | |
| 2002/0019649 A1 | 2/2002 | Sikora et al. | |
| 2002/0031551 A1 | 3/2002 | Peterson et al. | |
| 2002/0038151 A1 | 3/2002 | Plouhar et al. | |
| 2002/0048595 A1 | 4/2002 | Geistlich et al. | |
| 2002/0090725 A1 | 7/2002 | Simpson et al. | |
| 2002/0091444 A1 | 7/2002 | Yang | |
| 2002/0099448 A1 | 7/2002 | Hiles | |
| 2002/0173806 A1 | 11/2002 | Giannetti et al. | |
| 2003/0014126 A1 | 1/2003 | Patel et al. | |
| 2003/0021827 A1 | 1/2003 | Malaviya et al. | |
| 2003/0023316 A1 * | 1/2003 | Brown et al. | 623/23.72 |
| 2003/0032961 A1 | 2/2003 | Pelo et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0044444 A1 | 3/2003 | Malaviya et al. | |
| 2003/0049299 A1 | 3/2003 | Malaviya et al. | |
| 2003/0212447 A1 | 11/2003 | Euteneuer et al. | |
| 2004/0143344 A1 | 7/2004 | Malaviya et al. | |

FOREIGN PATENT DOCUMENTS

| | | |
|---|---|---|
| EP | 0591991 A2 | 4/1994 |
| EP | 0632999 A1 | 11/1995 |
| EP | 0 734 736 A1 | 10/1996 |
| EP | 1070487 | 1/2001 |
| EP | 1593400 A1 | 11/2005 |
| FR | 2422386 | 4/1978 |
| GB | 2 215 209 | 9/1989 |
| JP | 11319068 A | 11/1999 |
| WO | WO 90/09769 | 9/1990 |
| WO | WO 94/11008 | 5/1994 |
| WO | WO 95/05083 | 2/1995 |
| WO | WO 95/22301 | 8/1995 |
| WO | WO 95/06439 | 9/1995 |
| WO | WO 95/32623 | 12/1995 |
| WO | WO96/24304 | 8/1996 |
| WO | WO 96/24661 | 8/1996 |
| WO | WO 97/05193 A1 | 2/1997 |
| WO | WO 97/37613 | 10/1997 |
| WO | WO 98/06445 | 2/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 98/40111 | 9/1998 |
| WO | WO 99/03979 | 1/1999 |
| WO | WO 99/43786 | 9/1999 |
| WO | WO 99/47188 | 9/1999 |
| WO | WO 00/15765 | 3/2000 |
| WO | WO 00/16822 | 3/2000 |
| WO | WO 00/24437 A2 | 5/2000 |
| WO | WO 00/24437 A3 | 5/2000 |
| WO | WO 00/32250 | 6/2000 |
| WO | WO 00/48550 | 8/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |
| WO | WO 01/45765 | 6/2001 |
| WO | WO 01/66159 | 9/2001 |
| WO | WO 01/70293 A1 | 9/2001 |
| WO | WO 02/22184 | 3/2002 |
| WO | WO 03/007784 | 1/2003 |
| WO | WO 03/007788 A2 | 1/2003 |
| WO | WO 03/007790 A2 | 1/2003 |

OTHER PUBLICATIONS

Sandusky, et al., "Healing Comparison of Small Intestine Submucosa and ePTFE Grafts in the Canine Carotid Artery", *J. Surg.Res.*, 58:415-420, (1995).

Knapp, et al., "Biocompatibility of Small-Intestine Submucosa in Urinary Tract as Augmentation Cystoplasty Graft and Injectable Suspension", *J Endourology*, 8:125-130, (1994).

Kropp et al., "Regenerative Bladder Augmentation: A Review of the Initial Preclinical Studies with Porcine Small Intestinal Submucosa", *Muscle, Matrix, and Bladder Function*. Plenum Press, New York, (1995).

Kropp et al., "Experimental Assessment of Small Intestinal Submucosa as a Bladder Wall Substitute", *Urology* 446:396-400, (1995).

Vaught et al., "Detrusor Regeneration in the Rat Using Porcine Small Intestinal Submucosa Grafts: Functional Innervation and Receptor Expression", *J. Urol.*, 155:374-378, (1996).

Kropp et al, Characterization of Small Intestinal Submucosa Regenerated Canine Detrusor: Assessment of Reinnervation, In Vitro Compliance and contractility, *J. of Urol*,156:599-607, (1996).

Kropp et al., "Regenerative Urinary Bladder Augmentation Using Small Intestinal Submucosa: Urodynamic and Histopathologic Assessment in Long-Term Canine Bladder Augmentations", *Journal of Urology*, 155:2098-2104, (1996).

Aiken et al., "Small Intestinal Submucosa as an Intra-Articular Ligamentous Graft Material: A Pilot Study in Dogs", *Vet Comp Orthopedics Traumatology*, 7:124-128, (1994).

Badylak et al., "The Use of Xenogeneic Small Intestinal Submucosa as a Biomaterial for Achille's Tendon Repair in a dog model", *J Biomed Materials*, 29:977-985, (1995).

Hodde et al., "The Effect of Range of Motion Upon Remodeling of Small Intestinal Submucosa (SIS) when used as an Achilles Tendon Repair Material in the Rabbit", *Tissue Engineering* 3, 1:27-37, (1997).

Ferrand et al., "Directional Porosity of Porcine Small-Intestinal Submucosa", *J Biomed Materials Res*, 27:1235-1241, (1993).

Hiles et al., "Porosity of Porcine Small-Intestinal Submucosa for use as a Vascular Graft", *J Biomed Materials Res*, 27: 139-144, (1993).

Hodde et al., "Glycosaminoglycan Content of Small Intestinal Submucosa: A Bioscaffold for Tissue Replacement", *Tissue Engineering*, 2:3, 209-217, (1996).

Prevel et al., "Small Intestinal Submucosa: Utilization for Repair of Rodent Abdominal Wall Defects", *Ann Plast Surg*, 35:374-380, (1995).

Clarke et al., "Intestine Submucosa and Polypropylene Mesh for Abdominal Wall Repair in Dogs", *J Surg Res*, 60:107-114, (1996).

Prevel et al., "Small Intestinal Submucosa: Utilization as a Wound Dressing in Full-Thickness Rodent Wounds", *Ann Plast Surg*. 35:381-388, (1995).

Cobb et al., "Histology after Dural Grafting with Small Intestinal Submucosa", *Surgical Neurology*, 46: 389-394, (1996).

Cobb et al., "Porcine Small Intestinal Submucosa as a Dural Substitute", *Surgical Neurology*, 51:99-104, (1999).

Voytik-Harbin et al., "Application and Evaluation of the AlamarBlue Assay for Cell Growth and Survival of Fibroblasts", *Journal of Immunological Methods, In Vitro Cell Bio-Animal*, 34: 2399-246, (1998).

Suckow, M.A., "Enhanced Bone Regeneration Using Porcine Small Intestinal Submucosa", *J. Invest Surg*, 12: 277, (1999).

Badylak, S., et al., "Naturally Occurring Extracellular Matrix as a Scaffold for Musculoskeletal Repair", *Clin Orthop*, 3675:S333-S3433, (1999).

Cook, J.L. et al., "Induction of Meniscal Regeneration in Dogs Using a Novel Biomaterial", *Am J Sports Med*, 27: 658, (1999).

Dejardin, L.M. et al., "Use of small intestinal submucosal implants for regeneration of large fascial defects: an experimental study in dogs", *J Biomed Mater Res*, 46:203-211, (1999).

Sacks, M.S., et al., "Quantification of the fiber architecture and biaxial mechanical behavior of porcine intestinal submucosa", *J Biomed Mater Res*, 46:1-10, (1999).

Cook® News Releases, "Cook® Introduces Innovative Surgisis™ Soft Tissue Repair Biomaterial", (May 21, 2000).

Cook® News Releases, "Cook® Oasis™ Wound Dressing Biomaterial From Cook® Remodels Partial Thickness Skin Injuries", (Dec. 23, 1999).

Cook® News Releases, "Cook Incorporated Forms Dedicated Tissue Engineered Products Group", (Feb. 16, 2000).

Cook® News Releases, "FDA Clears Oasis™ Wound Dressing Biomaterial From Cook® For Full-Thickness Skin Injuries", (Jan. 24, 2000).

Klootwyk, et al., "The Use of Xenographic SIS as a Biomaterial for Achilles Tendon Repair in Dogs," *First SIS Symposium*, Dec. 1996, USA.

Lenz, et al., "SIS as an ACL Replacement in Dogs and Goats," *First Symposium*, Dec. 1996, USA.

Cook, et al., "Comparison of SIS Cancellous Bone as Substrates for Three-Dimensional Culture of Canine Articular Chondrocytes," *First SIS Symposium*, Dec. 1996, USA.

Badylak, et al., "Different Configurations of Small Intestinal Submucosa as a Biomaterial for Achilles Tendon Repair in a Dog Model," *First SIS Symposium*, Dec. 1996, USA.

Voytik-Harbin & Badylak, "Induction of Osteogenic Activity By Small Intestinal Submucosa in Rat Calvaria Non-union Defects," *First SIS Symposium*, Dec. 1996, USA.

Kandel, et al., "SIS and Reconstituted Cartilage and Its Use in Joint Resurfacing of Focal Defects in Rabbits," *First SIS Symposium*, Dec. 1996, USA.

Tullius, et al., "Differential Permeability of SIS," *First SIS Symposium*, Dec. 1996, USA.

Obermiller, et al., "Suture Retention Strength of SIS," *First SIS Symposium*, Dec. 1996, USA.

Shelton, et al., "Repair of the Canine Medial Meniscus using SIS: A Feasibility Study," *Second SIS Symposium*, Dec. 1998, USA.

Cook, et al., "Meniscal Regeneration in dogs Using Grafts of SIS," *Second SIS Symposium*, Dec. 1998, USA.

Welch, et al., "Healing of Canine Meniscal Defect with Small Intestinal Submucosa Implants," Dec. 1998, USA.

Solchaga, et al., "SIS as Delivery Vehicle for Mesenchymal Progenitor Cells," Dec. 1998, USA.

Paulino, et al., "The Use of an SIS-PGA Composite Graft for Repair of Cartilage Defect," Dec. 1998, USA.

Toombs and May, "Clinical Follow-Up of Three Canine ACL Reconstructions Using an SIS ACL Device," Dec. 1998, USA.

Tomasek and Gifford, "Small Intestinal Submucosa Matrix Regulates The Differentiation of Myofibroblasts," *Third SIS Symposium*, Nov. 2000, USA.

Cook, et al., "Tissue Engineering For Meniscal Repair Using SIS," *Third SIS Symposium*, Nov. 2000, USA.

Lifrak, et al., "Enhanced Repair of Goat Meniscal Defects Using Porcine Small Intestinal Submucosa (SIS)," *Third SIS Symposium*, Nov. 2000, USA.

Hoffman, "SIS Disc Replacement For the Temporomandibular Joint," *Third SIS Symposium*, Nov. 2000, USA.

Kaeding, "Use of SIS In The Surgical Treatment of Chronic Symptomatic Patella Tendinosis," *Third SIS Symposium*, Nov. 2000, USA.

Tomczak and Kaeding, "Use of SIS in The Surgical Treatment of Tendinosis About The Foot And Ankle," *Third SIS Symposium*, Nov. 2000, USA.

Moore, et al., "Bridging Segmental Defects In Long Bones With Intramedullary Tubes And Periosteal Sleeves Made From Small Intestinal Submucosa (SIS)," *Third SIS Symposium*, Nov. 2000, USA.

Wang, et al., "Small Intestinal Submucosa Enhances Healing of Medical Collateral Ligament In A Rabbit Model," *Third SIS Symposium*, Nov. 2000, USA.

Ojha, et al., "PGA-Plla Versus Small Intestinal Submucosa (SIS): A Comparison of Neo-Cartilage Grown From Two Scaffold Materials," *Third SIS Symposium*, Nov. 2000, USA.

Wiklerson, "Use of The Porcine Small Intestine Submucosal Tissue Graft And Repair of Rotator Cuff Tears," *Third SIS Symposium*, Nov. 2000, USA.

"Small Intestinal Submucosa," *Third SIS Symposium*, Nov. 2000, USA.

"Current Clinical Applications of SIS," *Third SIS Symposium*, Nov. 2000, USA.

Hodde, et al., "Glycosaminoglycan Content of Small Intestinal Submucosa: A Potential for GAG-Growth Interactions in SIS-Mediated Healing", *First Symposium*, Dec. 1996, USA.

Friess, "Collagen in drug delivery and tissue engineering", *Advanced Drug Delivery Reviews*, vol. 55, No. 12, 2003, pp. 1529-1530.

Olsen et al., "Recombinant collagen and gelatin for drug delivery", *Advanced Drug Delivery Reviews*, vol. 55, No. 12, 2003, pp. 1547-1567.

Aigner et al., "Collagens—major component of the physiological cartilage matrix, major target of cartilage degeneration, major tool in cartilage repair", *Advanced Drug Delivery Reviews*, vol. 55, No. 12, 2003, pp. 1569-1593.

Geiger et al., "Collagen sponges for bone regeneration with rhBMP-2", *Advanced Drug Delivery Reviews*, vol. 55, No. 12, 2003, pp. 1613-1629.

Ruszczak et al., "Collagen as a carrier for on-site delivery of antibacterial drugs", *Advanced Drug Delivery Reviews*, vol. 55, No. 12, 2003, pp. 1679-1698.

O'Grady et al., "Global regulatory registration requirements for collagen-based combination products: points to consider", *Advanced Drug Delivery Reviews*, vol. 55, No. 12, 2003, pp. 1699-1721.

Matthews et al., "Electrospinning of Collagen Type II: A Feasibility Study", *Journal of Bioactive and Compatible Polymers*, vol. 18, Mar. 2003, pp. 125-134.

Biscarini et al., "Growth of High Vacuum Sublimed Oligomer Thin Films", *ACS Polymer Preprints*, vol. 37, No. 2, 1996, pp. 618-619.

Biscarini et al., "Morphology and roughness of high-vacuum sublimed oligomer thin films", *Thin Solid Films*, vol. 439-443, 1996, pp. 284-285.

Biscarini et al., "Scaling Behavior of Anisotropic Organic Thin Films Grown in High-Vacuum", *Physical Review Letters*, vol. 78, No. 12, Mar. 24, 1997, pp. 2389-2392.

Voytik-Harbin et al., "Identification of Extractable Growth Factors from Small Intestinal Submucosa", *Journal of Cellular Biochemistry*, vol. 67, 1997, pp. 478-491.

McPherson, Ph.D. et al., "Characterization of Fibronectin Derived from Porcine Small Intestinal Submucosa", *Tissue Engineering*, vol. 4, No. 1, 1998, pp. 75-83.
Hodde, et al., "Vascular Endothelial Growth Factor in Porcine-Derived Extracellular Matrix", *Endothelium*, vol. 8(1), 2001, pp. 11-24.
Hodde et al., "Wounds: A Compendium of Clinical Research and Practice", *Website*: http:www.hmpcommunications.com/WNDS, Printed: Jul. 12, 2005, 7 pgs.
Hurst et al., "Mapping of the distribution of significant proteins and proteoglycans in small intestinal submucosa by fluorescence microscopy", *J. Biomater. Sci. Polymer Edn.*, vol. 12, No. 11, 2001, pp. 1267-1279.
Hodde et al., "Fibronectin peptides mediate HMEC adhesion to porcine-derived extracellular matrix", *Biomaterials*, vol. 23, 2002, pp. 1841-1848.
Hodde, "Naturally Occurring Scaffolds for Soft Tissue Repair and Regeneration", *Tissue Engineering*, vol. 8, No. 2, 2002, pp. 295-308.
Allman et al., Xenogeneic Extracellular Matrix Grafts Elicit a Th2-Restricted Immune Response, *Transplantation*, vol. 71, No. 11, Jun. 15, 2001, pp. 1631-1640.
Allman et al., "The Th2-Restricted Immune Response to Xenogeneic Small Intestinal Submucosa Does Not Influence Systemic Protective Immunity to Viral and Bacterial Pathogens", *Tissue Engineering*, vol. 8, No. 1, 2002, pp. 53-62.
Answers.com,. Definition of "freeze-dry", Accessed on May 12, 2005, 6 pgs.
Ma et al., "Microtubular architecture of biodegradable polymer scaffolds", *J. Biomed. Materials Res.*, vol. 56, No. 4, 2001, pp. 469-477.
Ma et al., "Biodegradable Polymer Scaffolds with Well-Defined Interconnected Spherical Pore Network", *Tissue Engineering*, vol. 7, No. 1, 2001, pp. 23-33.
Klawitter et al., "An Evaluation of Bone Growth into Porous High Density Polyethylene", *J. Biomed. Materials Res.*, vol. 10, (1976) pp. 311-323.
White et al., "Biomaterial Aspects of Interpore-200 Porous Hydroxyapatite", *Dental Clinics of North America*, Reconstructive Implant Surgery and Implant Prosthodontics 1, vol. 30, No. 1, pp. 49-67.
Shors, Coralline Bone Graft Substitutes, *Orthopaedic Clinics of North America*, Bone Grafting and Bone Graft Substitutes, vol. 30, No. 4, Oct. 1999, pp. 599-613.
Wang, Experimental Study of Osteogenic Activity of Sintered Hydroxyapatite—On the Relationship of Sintering Temperature and Pore Size-, *J. Jpn. Orthop. Assoc.*, vol. 64, 1990, pp. 847-859.
Nehrer et al., "Matrix collagen type and pore size influence behavior of seeded canine chondrocytes", *Biomaterials*, vol. 18, No. 11, 1997, pp. 769-776.
Salem et al., "Interactions of 3T3 fibroblasts and endothelial with defined pore ffeatures", *J. Biomed Materials Res.*, vol. 61, No. 2, 2002, pp. 212-217.
European Search Report for European Patent Application No. 05252559.9-2107, Sep. 22, 2005, 3 pgs.
Definitions of "intertwine" and "twine", *American Heritage Dictionary of the English Language Online*, Accessed Sep. 29, 2005, 2 pgs.
How to Cut Meat Products 2001, *Urschel Corp.*, Accessed online at fr.urschel.com/literature/HTCMeat.pdf on Oct. 3, 2005, 8 pgs.
Definitions of "comminute" and "slurry", *Dictionary.com*; Accessed Sep. 20, 2005, 2 pgs.
P. K. Chu et al., "Plasma-surface modification of biomaterials", *Materials Science and Engineering, Reports: A Review Journal*, vol. 36, No. 5-6, Mar. 29, 2002, pp. 143-206.
Arnoczky et al., The microvasculature of the meniscus and its response to injury—An experimental study in the dog, *Am. J. Sports Med.*, 1983, 11(3); pp. 131-141.
Fox et al., Trephination of incomplete meniscal tears, *Arthroscopy*, 1993, 9(4); pp. 451-455.
Arnoczky et al., Meniscal repair using an exogenous fibrin clot—An experimental study of dogs, *J. Bone Joint Surg. Am.*, 1988, 70(8), pp. 1209-1216.
Rodeo, "Arthroscopic meniscal repair with use of the outside-in technique", *Instr. Course Lect.*, 2000, 49, pp. 195-206.
Stollsteimer et al., "Meniscal allograft transplantation: a 1- to 5-year follow-up of 22 patients", *Arthroscopy*, 2000, 16(4), pp. 343-347.

Rodeo, "Meniscal allografts—where do we stand?", *Am. J. Sports Med.*, 2001, 29(2), pp. 246-261.
Sweigart et al., "Toward tissue engineering of the knee meniscus", *Tissue Eng.*, 2001, 7(2), pp. 111-129.
Boss et al., "Technical innovative: creation of a peripheral vascularized trough to enhance healing in cryopreserved meniscal allograft reconstruction", *Knee Surg Sports Traumatol Arthrosc.*, 2000, 8(3), pp. 159-162.
Siegel et al., "Meniscal allografts", *Clin Sports Med.*, 1993, 12(1), pp. 59-80.
Klompmaker et al., "Meniscal replacement using a porous polymer prosthesis: a preliminary study in the dog after dog.", *Biomaterials*, 1996, 17(12), pp. 1169-1175.
de Groot et al., "Use of porous polyurethanes for meniscal reconstruction and meniscal protheses", *Biomaterials*, 1996, 17(2), pp. 163-173.
Spaans et al., "Solvent-free fabrication of micro-porous polyurethane amide and polyurethane-urea scaffolds for repair and replacement of the knee-joint meniscus", *Biomaterials*, 2000, 21(23), pp. 2453-2460.
Stone et al., "Regeneration of meniscal cartilage with use of a collagen scaffold—Analysis of Preliminary date", *J. Bone Joint Surg. Am.*, 1997, 79(12), pp. 1770-1777.
Rodkey et al., "A clinical study of collagen meniscus implants to restore the injured meniscus", *Clin. Orthop.*, 1999, 49(367 Suppl.), pp. S281-S292.
Merriam-Webster Online Dictionary definitions of "suspension", "suspend", "cohesive", "cohesion", "comminute", "pulverize", "submucosa", and "tissue". Accessed Mar. 30, 2006, 9 pgs.
Resin Technology Group, LLC, "Viscosity chart", http://www.resintechgroup.com/tables/viscosity.html, accessed online Mar. 30, 2006, 1pg.
Definitions from Onelook.com for "trimethylen" and "trimethylene", accessed Mar. 17, 2006, 1 page.
J.S. Pieper et al "Preparation and characterization of porous crosslinked collagenous matrices containing bioavailable chondroitin suplhate" Biomaterials 1999, 20: 847-858.
P.B. van Wachem et al. "In vivo biocompatibility of carbodiimide-crosslinked collagen matrices: Effects of crosslink density, heparin immobilization, and bFGF loading" J. Biomed. Mater. Res. 2001, 55 (3): 368-378.
Kyumin Whang "A biodegradable polymer scaffold for delivery of osteotropic factors" Biomaterials 2000, 21 (24): 2545-2551.
J.S. Pieper et al. Attachment of glycosaminoglycans to collangenous matrices modulates the tissue response in rats, Biomaterials 2000, 21 (16): 1689-1699.
Kristen Billiar et al. "Effects of carbodiimide crosslinking conditions on the physical properties of laminated intestinal submucosa", J. Biomed. Mater. Res. 2001, 51(1): 101-108.
Toshimitsu Momose et al. "Surface modification of extrasynovial tendon by chemically modified hyaluronic acid coating" J. Biomed. Mater. Res. 2002, 59: 219-224.
Handbook of Biodegradable Polymers Hardwood Press 1997 (251-272).
Cohn et al., "Biodegradable PEO/PLA block copolymers," Journal of Biomedical Materials Research, 1988, 22 (993-1009).
"Polymer Preprints" (ACS Division of Polymer Chemistry), 1989. 30 (1): 498.
The Encyclopedia of Polymer Science, 1988 (13) 31-41.
"Handbook of Biodegradable Polymers" Hardwood Press 1977 (161-182).
"Handbook of Biodegradable Polymers" Hardwood Press 1997 (99-118).
Disilvestro et al., "Effects of Cross-Linking on the Mechanical Properties of a Porous Foam Scaffold of Small Intestine Submucosa", Society for Biomaterials 29th Annual Meeting Transactions, 2003, pp. 88.
Ide et al., "Collagen Hybridization with Poly(I-Lactic Acid) Braid Promotes Ligament Cell Migration", Mater. Sci. Eng. C, 17(1-2), 95-99 (2001).
Bercovy et al., "Carbon-PGLA Prosthesis for Ligament Reconstruction Experimental Basis and Short Term Results in Man", Clin. Orthop. Relat. Res., (196), 159-68 (1985).

Zhu et al, "Immobilization of Biomacromolecules onto Aminolyzed Poly(L-lactic acid) toward Acceleration of Endothelium Regeneration", Tissue Engineering, v 10, pp. 53-61, 2004.

Cheng & Teoh, "Surface modification of ultra thin poly (ÿ caprolactone) films using acrylic acid and collagen", Biomaterials, v25(11), pp. 1991-2001, 2004.

Wan et al., "Cell adhesion on gaseous plasma modified poly-(L-lactide) surface under shear stress field", Biomaterials, v24(21), pp. 3757-3764, 2003.

Yang et al., "Effect of surface treatment on the biocompatibility of microbial polyhydroxyalkanoates", Biomaterials, v 23 (5), pp. 1391-1397, 2002.

Croll et al., "Controllable surface modification of Poly(lactic-co-glycolic acid) (PLGA) by hydrolysis or aminolysis I: physical, chemical, and theoretical aspects", Biomacromolecules, Mar.-Apr. 2004, 5(2): 463-473.

Kwon et al., "Fibroblast culture on surface-modified poly (glycolide-co- ÿ-caprolactone) scaffold for soft tissue regeneration", J. Biomater Sci Polym ed. 2001, 12(10) 1147-60.

Gastel JA, Muirhead WR, Lifrak JT, Fadale PD, Hulstyn MJ, Labrador DP "Meniscal tissue regeneration using a collagenous biomaterial derived from porcine small intestine submucosa", Arthroscopy, February; 17(2): 151-159, 2001.

Tan W, Krishnaraj R, Desai TA "Evaluation of nanostructured composite collagen-chitosan matrices for tissue engineering", Tissue Eng April; 7(2): 203-210, 2001.

Arnoczky SP "Building a meniscus", Biological considerations, Clin Orthop October; 367 (suppl), S244-53, 1999.

Metcalf et al., "Surgical technique for xenograft (SIS) augmentation of rotator-cuff repairs", Op Tech Orthop, 12(3): 204-208, 2002.

Courtney et al., "Modification of polymer surfaces: optimization of approaches", Perfusion, v 18 (11), pp. 33-39, 2003.

Zhang et al., Design of nanostructured biological materials through self-assembly of peptides and proteins, MIT Current Opinion in chemical Biology, 2002, 6:865-871.

Hodde and Hiles, "Bioactive FGF-2 in sterilized extracellular matrix", Wounds, 13(5): 195-201 (2001).

Supplementary European Search Report, Appln No. 02753403.1 (PCT/US 223190) dated Dec. 21, 2006 (3 pages).

Definitions of "intertwine" and "twine." American Heritage Dictionary of the English Language Online. Accessed Sep. 29, 2005. 2 pages.

On-line Medical Dictionary definition of "extracellular matrix" located at http://cancerweb.nci.ac.uk/cgibin/omd?extracellular+matrix, Nov. 18, 1997, downloaded from internet on Nov. 27, 1996.

White et al., "Biomaterial Aspects of Interpore-200 Porous Hydroxyapatite", *Dental Clinics of North America*, Reconstructive Implant Surgery and Implant Prosthodontics 1, vol. 30, No. 1, pp. 49-67, 1986.

\* cited by examiner

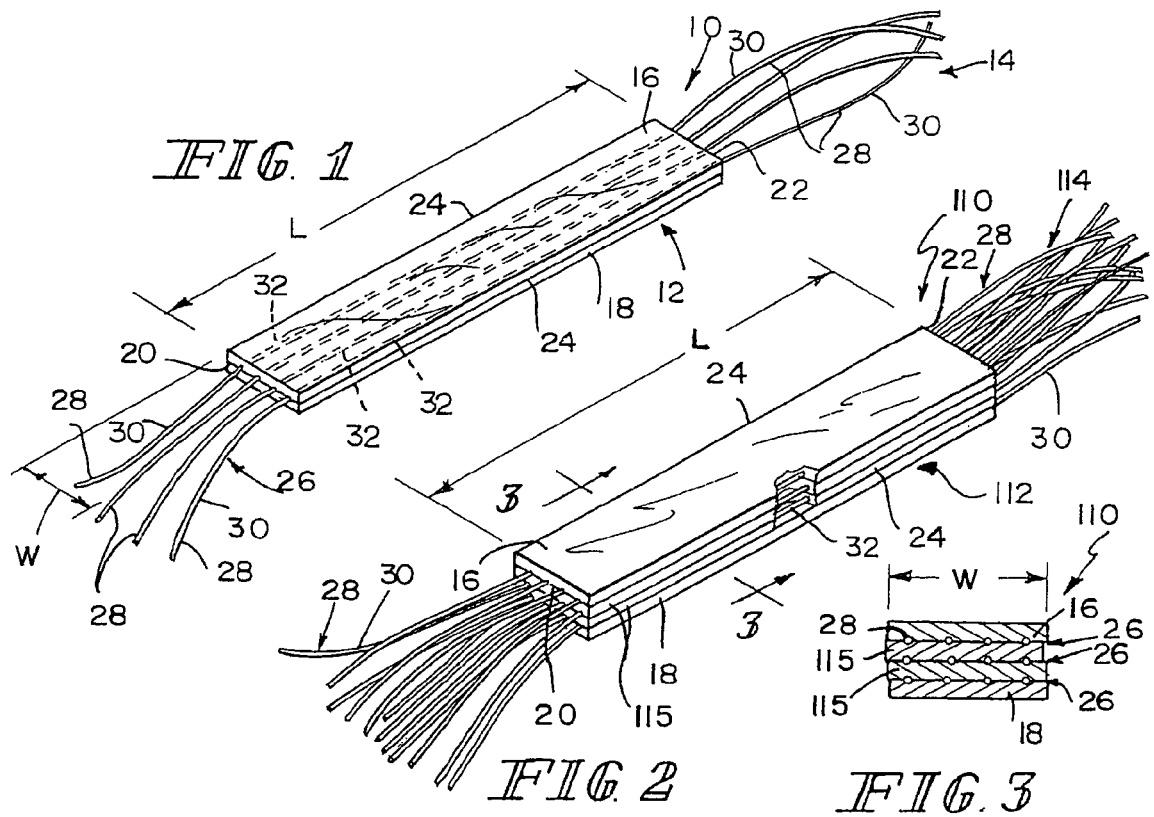
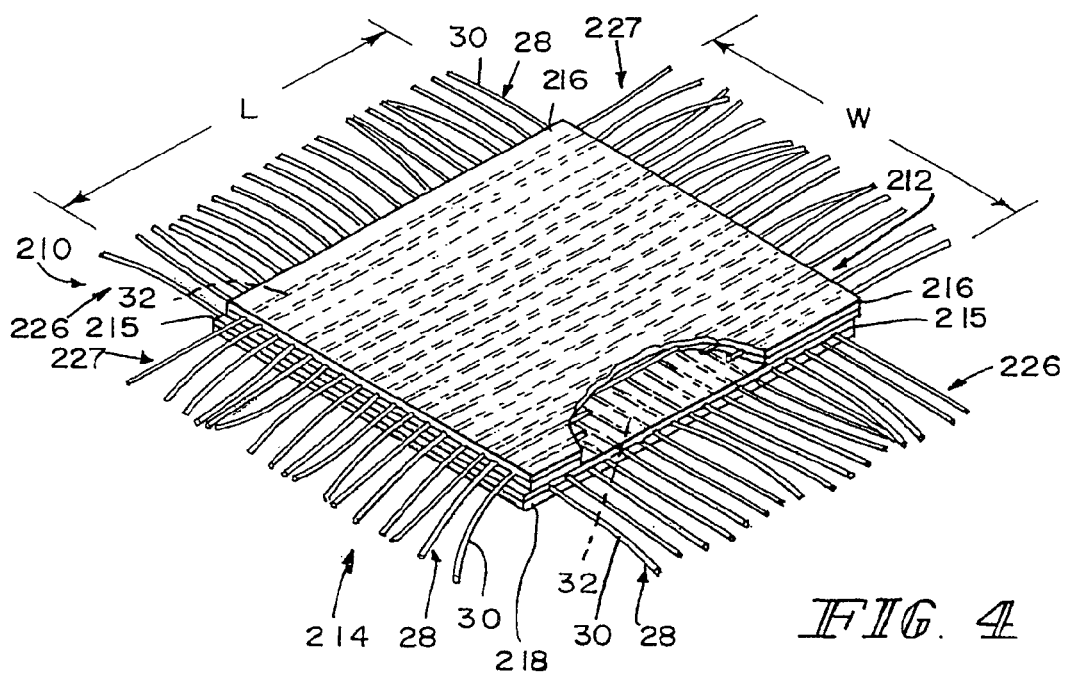

HYBRID BIOLOGIC-SYNTHETIC BIOABSORBABLE SCAFFOLDS

This application claims priority to U.S. Provisional Patent Application No. 60/567,886, filed May 4, 2004; and U.S. Provisional Patent Application No. 60/571,766, filed May 17, 2004. Both of these provisional patent applications are hereby incorporated by reference.

CROSS REFERENCE

Cross reference is made to U.S. patent application Ser. No. 10/195,794 entitled "Meniscus Regeneration Device and Method"; Ser. No. 10/195,719 entitled "Devices from Naturally Occurring Biologically Derived Materials"; Ser. No. 10/195,347 entitled "Cartilage Repair Apparatus and Method"; Ser. No. 10/195,344 entitled "Unitary Surgical Device and Method"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; and Ser. No. 10/195,633 entitled "Porous Delivery Scaffold and Method", each of which is assigned to the same assignee as the present application, each of which was filed on Jul. 15, 2002, and each of which is hereby incorporated by reference. Cross reference is also made to U.S. patent application Ser. No. 10/172,347 entitled "Hybrid Biologic-Synthetic Bioabsorbable Scaffolds" which was filed on Jun. 14, 2002 and U.S. patent application Ser. No. 10/195,341 entitled "Hybrid Biologic/Synthetic Porous Extracellular Matrix Scaffolds" which was filed on Jul. 15, 2002, both of which are assigned to the same assignee as the present application, and which are hereby incorporated by reference.

Cross reference is also made to U.S. patent application Ser. No. 11/110,532 entitled "Hybrid Biologic-Synthetic Bioabsorbable Scaffolds" which was filed concurrently herewith, is assigned to the same assignee as the present application, is now abandoned and is hereby incorporated by reference.

FIELD OF THE INVENTION

The present invention relates to bioprosthetics and particularly to the use of bioprosthetics for the repair and replacement of connective tissue. More particularly, the present invention relates to the use of a composite bioprosthetic device made up of a synthetic portion and heterologous animal tissue.

BACKGROUND AND SUMMARY OF THE INVENTION

Currently there are multiple patents and publications which describe in detail the characteristics and properties of small intestine submucosa (SIS). See, for example, U.S. Pat. Nos. 4,352,463, 4,902,508, 4,956,179, 5,281,422, 5,372,821, 5,445,833, 5,516,533, 5,573,784, 5,641,518, 5,645,860, 5,668,288, 5,695,998, 5,711,969, 5,730,933, 5,733,868, 5,753,267, 5,755,791, 5,762,966, 5,788,625, 5,866,414, 5,885,619, 5,922,028, 6,056,777, and WO 97/37613, incorporated herein by reference. SIS, in various forms, is commercially available from Cook Biotech Incorporated (Bloomington, Ind.). Further, U.S. Pat. No. 4,400,833 to Kurland and PCT publication having International Publication Number WO 00/16822 provide information related to bioprosthetics and are also incorporated herein by reference.

It is also known to use naturally occurring extracellular matrices (ECMs) to provide a scaffold for tissue repair and regeneration. One such ECM is small intestine submucosa (SIS). SIS has been used to repair, support, and stabilize a wide variety of anatomical defects and traumatic injuries. Commercially-available SIS material is derived from porcine small intestinal submucosa that remodels the qualities of its host when implanted in human soft tissues. Further, it is taught that the SIS material provides a natural matrix with a three-dimensional microstructure and biochemical composition that facilitates host cell proliferation and supports tissue remodeling. SIS products, such as Oasis material and Surgisis material, are commercially available from Cook Biotech, Bloomington, Ind.

An SIS product referred to as RESTORE Orthobiologic Implant is available from DePuy Orthopaedics, Inc. in Warsaw, Indiana. The DePuy product is described for use during rotator cuff surgery, and is provided as a resorbable framework that allows the rotator cuff tendon to regenerate itself. The RESTORE Implant is derived from porcine small intestine submucosa that has been cleaned, disinfected, and sterilized. Small intestine submucosa (SIS) has been described as a naturally-occurring ECM composed primarily of collagenous proteins. Other biological molecules, such as growth factors, glycosaminoglycans, etc., have also been identified in SIS. See Hodde et al., Tissue Eng. 2(3): 209-217 (1996); Voytik-Harbin et al., J. Cell Biochem., 67:478-491 (1997); McPherson and Badylak, Tissue Eng., 4(1): 75-83 (1998); Hodde et al., Endothelium, 8(1):11-24 (2001); Hodde and Hiles, Wounds, 13(5): 195-201 (2001); Hurst and Bonner, J. Biomater. Sci. Polym. Ed., 12(11) 1267-1279 (2001); Hodde et al., Biomaterial, 23(8): 1841-1848 (2002); and Hodde, Tissue Eng., 8(2): 295-308 (2002), all of which are incorporated by reference herein. During seven years of preclinical testing in animals, there were no incidences of infection transmission from the implant to the host, and the SIS material has not decreased the systemic activity of the immune system. See Allman et al., Transplant, 17(11): 1631-1640 (2001); Allman et al., Tissue Eng., 8(1): 53-62 (2002).

While small intestine submucosa is available, other sources of submucosa are known to be effective for tissue remodeling. These sources include, but are not limited to, stomach, bladder, alimentary, respiratory, or genital submucosa, or liver basement membrane. See, e.g., U.S. Pat. Nos. 6,379,710, 6,171,344, 6,099,567, and 5,554,389, hereby incorporated by reference. Further, while SIS is most often porcine derived, it is known that these various submucosa materials may be derived from non-porcine sources, including bovine and ovine sources. Additionally, the ECM material may also include partial layers of laminar muscular is mucosa, muscular is mucosoa, lamina propria, stratum compactum and/or other tissue materials depending upon factors such as the source from which the ECM material was derived and the delamination procedure.

For the purposes of this invention, it is within the definition of a naturally occurring ECM to clean, delaminate, and/or comminute the ECM, or even to cross-link the collagen fibers within the ECM. It is also within the definition of naturally occurring ECM to fully or partially remove one or more sub-components of the naturally occurring ECM. However, it is not within the definition of a naturally occurring ECM to separate and purify the natural collagen or other components or sub-components of the ECM and reform a matrix material from the purified natural collagen or other components or sub-components of the ECM. While reference is made to SIS, it is understood that other naturally occurring ECMs (e.g., stomach, bladder, alimentary, respiratory, and genital submucosa, and liver basement membrane), whatever the source (e.g., bovine, porcine, ovine) are within the scope of this disclosure. Thus, in this application, the terms "naturally occurring extracellular matrix" or "naturally occurring ECM" are intended to refer to extracellular matrix material that has been cleaned, disinfected, sterilized, and optionally cross-linked. The terms "naturally occurring extracellular matrix" and "naturally occurring ECM" are also intended to include ECM foam material prepared as described in U.S. Patent Application No. 60/388,761 entitled "Extracellular Matrix Scaffold and Method for Making the Same".

There are currently many ways in which various types of tissues such as ligaments and tendons, for example, are reinforced and/or reconstructed. Suturing the torn or ruptured ends of the tissue is one method of attempting to restore function to the injured tissue. Sutures may also be reinforced through the use of synthetic non-bioabsorbable or bioabsorbable materials. Autografting, where tissue is taken from another site on the patient's body, is another means of soft tissue reconstruction. Yet another means of repair or reconstruction can be achieved through allografting, where tissue from a donor of the same species is used. Still another means of repair or reconstruction of soft tissue is through xenografting in which tissue from a donor of a different species is used.

According to the present invention, a bioprosthetic device for soft tissue attachment, reinforcement, and/or reconstruction is provided. The bioprosthetic device comprises SIS or other ECM formed to include a tissue layer, and a synthetic portion coupled to the tissue layer. The tissue layer may also be dehydrated.

In one embodiment, the SIS portion of the bioprosthetic device includes a top tissue layer of SIS material and a bottom tissue layer of SIS material coupled to the top tissue layer. The synthetic portion of the bioprosthetic device includes a row of fibers positioned to lie between the top and bottom tissue layers of the SIS portion. The fibers are positioned to lie in a spaced-apart coplanar relation to one another along a length, L, of the SIS portion. The fibers are each formed to include a length L2, where L2 is longer than L so that an outer end portion of each fiber extends beyond the SIS portion in order to anchor the bioprosthetic device to the surrounding soft tissue.

Illustratively, in another embodiment, the synthetic reinforcing portion of the bioprosthetic device includes a mesh member formed to define the same length, L, as the SIS portion, or may include a mesh member having a body portion coupled to the SIS portion and outer wing members coupled to the body portion and positioned to extend beyond the length, L, and a width, W, of the SIS portion in order to provide more material for anchoring the bioprosthetic device to the surrounding soft tissue.

The synthetic reinforcing portion of the device enhances the mechanical integrity of the construct in one (for fiber reinforcements) or two (for fiber or mesh reinforcements) dimensions. For the repair of tissues such as meniscal or articular cartilage, or discs, integrity in three dimensions is desirable for the implant to withstand the shear forces that will be present after implantation. Thus, in one embodiment of the present application, the absorbable synthetic portion of the device is in a three-dimensional form, to provide mechanical strength in three dimensions. The absorbable synthetic may be a fibrous nonwoven construct or a three-dimensional woven mesh, for example.

For the repair of certain other types of tissues such as tendons, ligaments, or fascia, tissue infiltration and repair in three dimensions is desirable, although three-dimensional enhanced mechanical integrity of the implant is not necessary. Thus, another embodiment of this invention is a composite device comprised of an SIS portion and an absorbable synthetic foam. The absorbable synthetic foam, in one example, is made of a biocompatible polymer that has a degradation profile that exceeds that of the SIS portion of the device. In this case, the SIS portion of the device provides the initial suturability of the product, and the synthetic foam provides an increased surface area in three dimensions for enhanced tissue infiltration. In a further embodiment, that synthetic foam is made of 65/35 polyglycolic acid/polycaprolactone, or 60/40 polylactic acid/polycaprolactone, or a 50:50 mix of the two.

The ECM portion of the composite may be provided as a single, hydrated sheet of SIS. Alternatively, the single sheet of SIS is lyophilized (freeze-dried). Such a treatment renders increased porosity to the SIS sheet, thereby enhancing it's capacity for allowing tissue ingrowth. Additionally, this SIS portion may comprise multiple sheets of SIS that have been laminated together by mechanical pressure while hydrated. The laminated SIS assembly optionally further physically crosslinked by partially or fully drying (down to less than 15% moisture content) under vacuum pressure. Alternatively, the laminated SIS assembly is lyophilized, instead of being vacuum dried, to increase its porosity. In still another embodiment, the SIS sheet or laminate is perforated by mechanical means, to create holes ranging, for example, from 1 mm to 1 cm. Another embodiment uses woven textiles of single or multi-layer SIS strips that have been optionally vacuum dried or lyophilized, to create meshes having different-sized openings. The woven mesh SIS optionally is assembled while the SIS is still hydrated and then the whole assembly vacuum-dried or lyophilized. Such a construct is suturable in the short term, and has the advantage of having a very open structure for tissue ingrowth over time.

The three-dimensional synthetic portion of the device is illustratively provided in the form of a fibrous nonwoven or foam material. The synthetic portion of the device preferably has interconnecting pores or voids to facilitate the transport of nutrients and/or invasion of cells into the scaffold. The interconnected voids range in size, for example, from about 20 to 400 microns, preferably 50 to 250 microns, and constitute about 70 to 95 percent of the total volume of the construct. The range of the void size in the construct can be manipulated by changing process steps during construct fabrication. The foam optionally may be formed around a reinforcing material, for example, a knitted mesh.

The synthetic reinforcing portion of the device is made of a fibrous matrix made, for example, of threads, yarns, nets, laces, felts, and nonwovens. An illustrated method of combining the bioabsorbable fibrous materials, e.g. fibers, to make the fibrous matrix for use in devices of the present invention is known to one skilled in the art as the wet lay process of forming nonwovens. The wet lay method has been described in "Nonwoven Textiles," by Radko Krcma, Textile Trade Press, Manchester, England, 1967 pages 175-176.

Alternatively, the synthetic reinforcing portion of the device is made of a three-dimensional mesh or textile. A preferred method of combining the bioabsorbable fibrous materials, e.g. fibers, to make the fibrous matrix for use in devices of the present invention is known to one skilled in the art as three-dimensional weaving or knitting. The three-dimensional weaving/knitting or braiding method has been described by several groups who have used the constructs for tissue engineering applications including Chen et al. in "Collagen Hybridization with Poly(1-Lactic Acid) Braid Promotes Ligament Cell Migration," Mater. Sci. Eng. C, 17(1-2), 95-99(2001), and Bercovy et al., in "Carbon-PLGA Prostheses for Ligament Reconstruction Experimental Basis and Short Term Results in Man," Clin. Orthop. Relat. Res., (196), 159-68(1985). Such a three-dimensional material can provide both reinforcement and three-dimensional form.

The synthetic reinforcing portion of the tissue implant of the present invention may include textiles with woven, knitted, warped knitted (i.e., lace-like), nonwoven, and braided structures. In an exemplary embodiment the reinforcing component has a mesh-like structure. However, in any of the above structures, mechanical properties of the material can be altered by changing the density or texture of the material. The fibers used to make the reinforcing component can be for example, monofilaments, yarns, threads, braids, or bundles of fibers. These fibers can be made of any biocompatible material, including bioabsorbable materials such as polylactic acid (PLA), polyglycolic acid (PGA), polycaprolactone (PCL), polydioxanone (PDO), trimethylene carbonate (TMC), polyvinyl alcohol (PVA), copolymers or blends thereof. In an exemplary embodiment, the fibers that comprise the nonwoven or three-dimensional mesh are formed of a polylactic acid and polyglycolic acid copolymer at a 95:5 mole ratio.

The ECM and the synthetic three-dimensional portion are provided in layers. It is understood for the purposes of this invention that the term "coupled to" describes a relationship wherein a surface of one layer is in contact with a surface of another layer and the two surfaces are connected through mechanical or chemical means, such as through lamination, crosslinking, diffusion of the material of one layer into interstices of the adjacent layer, stitching, and the like. "Sandwiched between" describes a relationship wherein a middle layer has a first surface in contact with a surface of an adjacent layer, and a second opposite-facing surface in contact with a surface of a second adjacent layer. Again, it is understood that the sandwiched layers are connected through mechanical or chemical means. The synthetic reinforcing portion may be provided as individual fibers or as layers. The synthetic reinforcing portion may be imbedded within a foam layer, provided between two other layers that are otherwise coupled together, or may form a layer that is coupled to one or more adjacent layers.

It is anticipated that the devices of the present invention can be combined with one or more bioactive agents (in addition to those already present in naturally occurring ECM), one or more biologically-derived agents or substances, one or more cell types, one or more biological lubricants, one or more biocompatible inorganic materials, one or more biocompatible synthetic polymers and one or more biopolymers. Moreover, the devices of the present invention can be combined with devices containing such materials.

"Bioactive agents" include one or more of the following: chemotactic agents; therapeutic agents (e.g. antibiotics, steroidal and non-steroidal analgesics and anti-inflammatories, anti-rejection agents such as immunosuppressants and anti-cancer drugs); various proteins (e.g. short chain peptides, bone morphogenic proteins, glycoprotein and lipoprotein); cell attachment mediators; biologically active ligands; integrin binding sequence; ligands; various growth and/or differentiation agents (e.g. epidermal growth factor, IGF-I, IGF-II, TGF-β I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; $TGF_\beta$ superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. If other such substances have therapeutic value in the orthopaedic field, it is anticipated that at least some of these substances will have use in the present invention, and such substances should be included in the meaning of "bioactive agent" and "bioactive agents" unless expressly limited otherwise.

"Biologically derived agents" include one or more of the following: bone (autograft, allograft, and xenograft) and derivates of bone; cartilage (autograft, allograft, and xenograft), including, for example, meniscal tissue, and derivatives; ligament (autograft, allograft, and xenograft) and derivatives; derivatives of intestinal tissue (autograft, allograft, and xenograft), including for example submucosa; derivatives of stomach tissue (autograft, allograft, and xenograft), including for example submucosa; derivatives of bladder tissue (autograft, allograft, and xenograft), including for example submucosa; derivatives of alimentary tissue (autograft, allograft, and xenograft), including for example submucosa; derivatives of respiratory tissue (autograft, allograft, and xenograft), including for example submucosa; derivatives of genital tissue (autograft, allograft, and xenograft), including for example submucosa; derivatives of liver tissue (autograft, allograft, and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the present invention, and such substances should be included in the meaning of "biologically-derived agent" and "biologically-derived agents" unless expressly limited otherwise.

"Biologically derived agents" also include bioremodelable collageneous tissue matrices. The expressions "bioremodelable collagenous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, tendon, whatever the source. Although "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers. The term "bioremodelable collageneous tissue matrices" includes "extracellular matrices" within its definition.

"Cells" include one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells;

a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited otherwise. Illustratively, in one example of embodiments that are to be seeded with living cells such as chondrocytes, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential amino acids, glucose, ascorbic acid, sodium pyrovate, fungicides, antibiotics, etc., in concentrations deemed appropriate for cell type, shipping conditions, etc.

"Biological lubricants" include: hyaluronic acid and its salts, such as sodium hyaluronate; glycosaminoglycans such as dermatan sulfate, heparan sulfate, chondroiton sulfate and keratan sulfate; synovial fluid and components of synovial fluid, including mucinous glycoproteins (e.g. lubricin), tribonectins, articular cartilage superficial zone proteins, surface-active phospholipids, lubricating glycoproteins I, II; vitronectin; and rooster comb hyaluronate. "Biological lubricant" is also intended to include commercial products such as ARTHREASE™ high molecular weight sodium hyaluronate, available in Europe from DePuy International, Ltd. of Leeds, England, and manufactured by Bio-Technology General (Israel) Ltd., of Rehovot, Israel; SYNVISC® Hylan G-F 20, manufactured by Biomatrix, Inc., of Ridgefield, N.J. and distributed by Wyeth-Ayerst Pharmaceuticals of Philadelphia, Pa.; HYLAGAN® sodium hyaluronate, available from Sanofi-Synthelabo, Inc., of New York, N.Y., manufactured by FIDIA S.p.A., of Padua, Italy; and HEALON® sodium hyaluronate, available from Pharmacia Corporation of Peapack, N.J. in concentrations of 1%, 1.4% and 2.3% (for opthalmologic uses). If other such substances have therapeutic value in the orthopaedic field, it is anticipated that at least some of these substances will have use in the present invention, and such substances should be included in the meaning of "biological lubricant" and "biological lubricants" unless expressly limited otherwise.

"Biocompatible polymers" is intended to include both synthetic polymers and biopolymers (e.g. collagen). Examples of biocompatible polymers include: polyesters of [alpha]-hydroxycarboxylic acids, such as poly(L-lactide) (PLLA) and polyglycolide (PGA); poly-p-dioxanone (PDO); polycaprolactone (PCL); polyvinyl alcohol (PVA); polyethylene oxide (PEO); polymers disclosed in U.S. Pat. Nos. 6,333,029 and 6,355,699; and any other bioresorbable and biocompatible polymer, co-polymer or mixture of polymers or co-polymers that are utilized in the construction of prosthetic implants. In addition, as new biocompatible, bioresorbable materials are developed, it is expected that at least some of them will be useful materials from which orthopaedic devices may be made. It should be understood that the above materials are identified by way of example only, and the present invention is not limited to any particular material unless expressly called for in the claims.

"Biocompatible inorganic materials" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphate, sintered and non-sintered ceramic particles, and combinations of such materials. If other such substances have therapeutic value in the orthopaedic field, it is anticipated that at least some of these substances will have use in the present invention, and such substances should be included in the meaning of "biocompatible inorganic material" and "biocompatible inorganic materials" unless expressly limited otherwise.

It is expected that various combinations of bioactive agents, biologically derived agents, cells, biological lubricants, biocompatible inorganic materials, biocompatible polymers can be used with the devices of the present invention.

Thus, in one aspect of this invention a bioprosthetic device is provided comprising a layer of ECM material having a first surface, and a three-dimensional synthetic portion having a first surface, wherein the first surface of the ECM layer is coupled to the first surface of the three-dimensional synthetic portion. The three-dimensional synthetic portion may be a fibrous material, illustratively selected from the group consisting of mesh, textile, and felt. Alternatively, the three-dimensional synthetic portion may be a synthetic foam.

In another aspect of this invention a prosthetic device is provided comprising one or more layers of bioremodelable collageneous tissue matrices material coupled to one or more three-dimensional synthetic bodies to provide a three-dimensional composite for tissue attachment, reinforcement, or reconstruction.

In yet another aspect of this invention, a method for making a bioprosthetic device is provided, the method comprising the steps of providing a layer of ECM material having a first surface, placing a polymer solution in contact the first surface of the ECM material to make an assembly, wherein the polymer is selected to form a foam upon lyophilization, and lyophilizing the assembly.

Additional features of the present invention will become apparent to those skilled in the art upon consideration of the following description of preferred embodiments of the invention exemplifying the best mode of carrying out the invention as presently perceived.

BRIEF DESCRIPTION OF THE DRAWINGS

The detailed description particularly refers to the accompanying figures in which:

FIG. 1 is a perspective view showing a composite bioprosthetic device of the present invention formed to include a small intestinal submucosa (SIS) portion and a synthetic portion and showing the SIS portion including a top tissue layer of SIS material and a bottom tissue layer of SIS material and further showing the synthetic portion including a row of four fibers positioned to lie in coplanar relation to each other between the top and bottom tissue layers of the SIS portion and positioned to run longitudinally along a length of the SIS portion and extend beyond a first and second end of the SIS portion in order to anchor the bioprosthetic device to surrounding soft tissue;

FIG. 2 is a perspective view similar to FIG. 1 showing an SIS portion of another bioprosthetic device of the present invention being formed to include a top layer, a bottom layer, and two middle layers positioned to lie between the top and the bottom layers and a synthetic device being formed to include three rows of four fibers so that each row is positioned to lie between each of the adjacent tissue layers of the SIS portion so that each fiber is positioned to run longitudinally along a length, L, of the SIS portion;

FIG. 3 is a sectional view taken along line 3-3 of FIG. 2 showing the top, bottom, and middle tissue layers of the SIS portion and also showing the three rows of fibers of the synthetic portion of the bioprosthetic device;

FIG. 4 is a perspective view showing an SIS portion of yet another bioprosthetic device of the present invention being formed to include four tissue layers, similar to FIG. 2, and also showing a synthetic portion of the bioprosthetic device including a first row of multiple fibers positioned to lie between two tissue layers of the SIS portion along a length, L, of the SIS portion and a second row of multiple fibers positioned to lie between two other tissue layers of the SIS portion along a width, W, of the SIS portion;

DETAILED DESCRIPTION OF THE DRAWINGS

Figure 5:
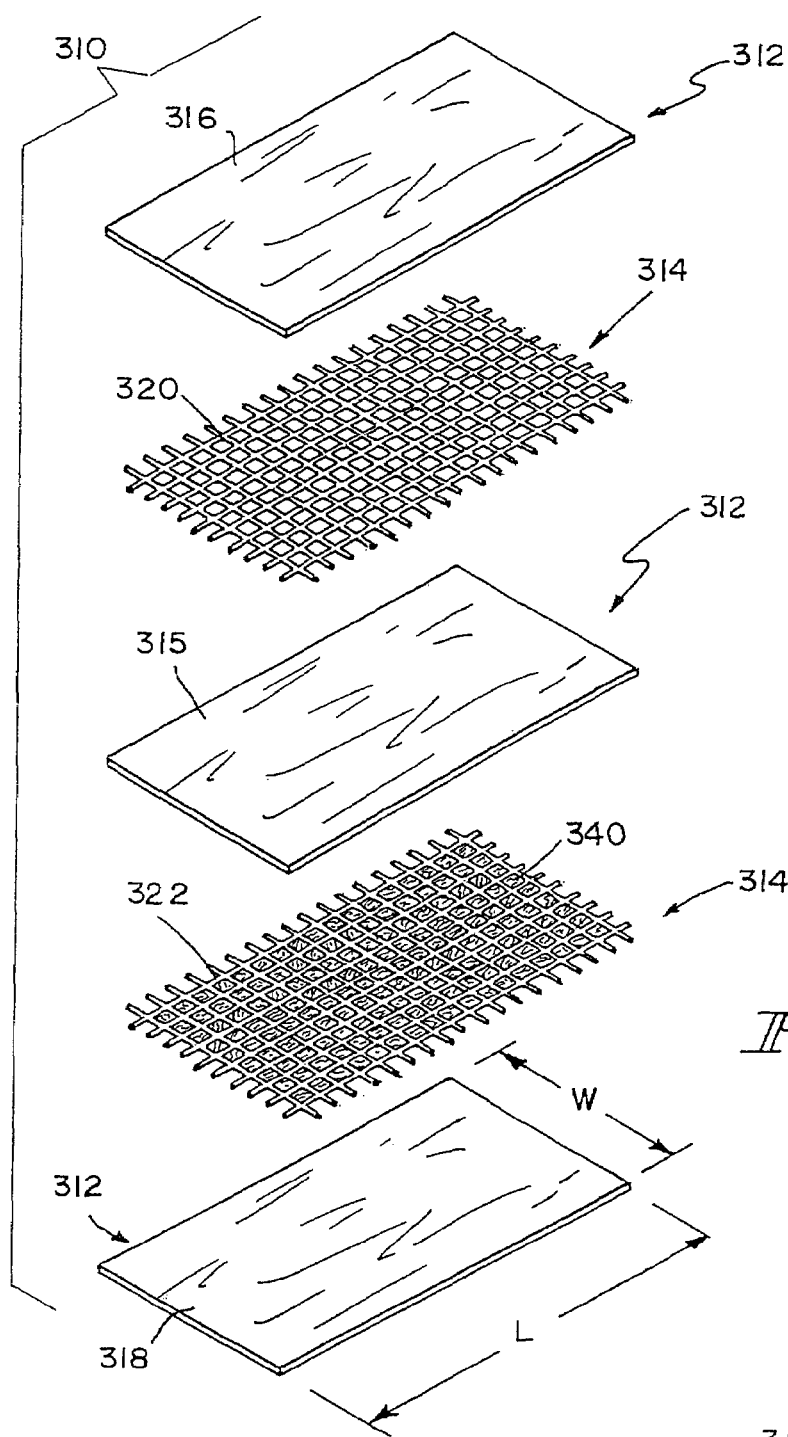
FIG. 5 is an exploded perspective view of another bioprosthetic device of the present invention showing an SIS portion of the prosthetic device including top, bottom, and middle tissue layers and showing a synthetic portion including a first and a second mesh member positioned to lie between the top and middle tissue layers of and the middle and bottom tissue layers of the SIS portion, respectively.

A composite bioprosthetic device 10, as shown in FIG. 1, is provided for the purposes of soft tissue attachment, reinforcement, and/or reconstruction. Bioprosthetic device 10 includes a small intestinal submucosa (SIS) portion 12 and a synthetic portion 14. SIS portion 12 is provided to be absorbed into the body and replaced by host tissue. SIS portion 12 acts as a scaffold for tissue ingrowth and remodeling. Synthetic portion 14 of bioprosthetic device 10 provides additional initial mechanical strength to bioprosthetic device 10. Because device 10 includes SIS portion 12 and synthetic portion 14, bioprosthetic device 10 is provided with a differential in biodegradation and bioremodeling rates. Synthetic portion 14, for example, can be configured to degrade at a slower rate than SIS portion 12. Further, synthetic portion 14 may act as an anchor to couple bioprosthetic device 10 to the surrounding soft tissue (not shown) during surgery. Alternatively, the SIS portion may be sutured to couple the bioprosthetic device to the surrounding tissue.

SIS portion 12 of bioprosthetic device 10, as shown in FIG. 1, includes a top tissue layer 16 and a bottom tissue layer 18 coupled to top tissue layer 16 mechanically or through a dehydration process. Although top and bottom tissue layers 16, 18 are provided in bioprosthetic device 10 shown in FIG. 1, it is within the scope of this disclosure, as will be described in more detail later, to include SIS portions 12 having any number of tissue layers. It is also included within the scope of this disclosure to provide perforated tissue layers or any other physical configuration of SIS. See FIGS. 2-4, for example. Further, it is within the scope of this disclosure to define top and bottom tissue layers 16, 18 as including multiple tissue layers each. In preferred embodiments, for example, top and bottom tissue layers 16, 18 each include three to four layers of SIS tissue. SIS portion 12 further includes a first end 20, a second end 22 spaced-apart from first end 20, and sides 24 coupled to and positioned to lie between first and second ends 20, 22. A length, L, is defined as the distance between first end 20 and second end 22 and a width, W, is defined as the distance between sides 24.

Synthetic portion 14 of bioprosthetic device 10 includes row 26 of four fibers 28, as shown in FIG. 1. It is within the scope of the disclosure to define fibers to include fibers or any fibrous material. Fibers 28 are positioned to lie along length L between top and bottom tissue layers 16, 18 and are further positioned to lie in coplanar relation to one another. When making bioprosthetic device 10, fibers 28 of synthetic portion 14 are placed between top and bottom tissue layers 16, 18 prior to dehydration. Although row 26 of four fibers 28 is provided in bioprosthetic device 10 shown in FIG. 1, it is within the scope of this disclosure to include synthetic portions 14 formed to include any number of rows 26 having any number of fibers 28. It is further within the scope of this disclosure to include fibers 28 made from bioabsorbable and non-bioabsorbable materials. For example, it is within the scope of this disclosure to include fibers 28 made from polylactic acid (PLA) or polyglycolic (PGA) acid, a combination of the two, Panacryl™ absorbable suture (Ethicon, Inc, Somerville, N.J.), other bioabsorbable materials, nylon, polyethylene, Kevlar™, Dacron™, PTFE, carbon fiber, or other non-bioabsorbable materials.

As shown in FIG. 1, each fiber 28 of bioprosthetic device 10 includes two outer end portions 30 a middle portion 32 coupled to and positioned to lie between outer end portions 30. Middle portion 32 is positioned to lie between top tissue layer 16 and bottom tissue layer 18 of SIS portion 12. Middle portion 32 of fibers 28 helps to provide strength along length, L, of bioprosthetic device 10. One or more outer end portions 30 of fibers 28 can be used for anchoring bioprosthetic device 10 to surrounding soft tissue (not shown). The combination of SIS portion 12 and fibers 28 further provide bioprosthetic device 10 with differential biodegradation rates. For example, fibers 28 of synthetic portion 14 can be made to be non-bioabsorbable or can be made with material which absorbs into the body at a slower rate than SIS portion 12. Uses for bioprosthetic device 10 shown in FIG. 1 include, but are not limited to, ligament or tendon repair.

An alternate bioprosthetic device 110 is shown in FIGS. 2 and 3. Bioprosthetic device 110 include an alternate SIS portion 112 of having top tissue layer 16, bottom tissue layer 18, and two middle tissue layers 115. Top, bottom, and middle tissue layers 16, 18, 115 include one or more layers of SIS tissue each. SIS portion 112, similar to SIS portion 12, also includes a first end 20, a second end 22 spaced-apart from first end 20, and sides 24. Bioprosthetic device 110 further includes an alternate synthetic portion 114 having three rows 26 of four fibers 28. One row 26 is positioned to lie between top tissue layer 16 and one of the middle tissue layers 115. Another row 26 is positioned to lie between the two middle tissue layers 115, and the final row 26 of fibers 28 is positioned to lie between another one of the middle tissue layers 115 and bottom tissue layer 16, as shown in FIG. 3. Fibers 28 of bioprosthetic device 110, similar to fibers 28 of bioprosthetic device 10, are positioned to lie along length, L, of SIS portion 112.

Although fibers 28 of bioprosthetic devices 10, 110 are positioned to lie along length, L, of each respective SIS portion 12, 112, it is within the scope of this disclosure to include a synthetic portion 214 of an alternate bioprosthetic device 210, as shown in FIG. 4, having multi-directional fibers 28 positioned to lie along a length, L, of an SIS portion 212 and along width, W, of SIS portion 212. Synthetic portion 214 of bioprosthetic device 210 includes a first row 226 having seventeen fibers 28 positioned to lie along length, L, of SIS portion 212. Synthetic portion 214 further includes a second row 227 having eighteen fibers 28 positioned to lie along width, W, of SIS portion 212 so that the fibers 28 of first row 226 and second row 227 are positioned to lie orthogonally with respect to each other. Although rows 226 and 227 are positioned to lie in orthogonal relation to one another, it is within the scope of this disclosure to include synthetic portion 214 having first and second rows 226 and 227 which lie at any angular relation to one another. It is also within the scope of this disclosure to include rows 226 and 227 each having any number of fibers 28.

Similar to bioprosthetic device 110 shown in FIG. 2, bioprosthetic device 210 includes a top tissue layer 216, a bottom tissue layer 218, and two middle tissue layers 215, positioned to lie between top and bottom tissue layers 216, 218. As mentioned before, top, bottom, and middle tissue layers 216, 218, 215 are each formed to include one or more layers of SIS tissue. Although SIS portion 212 of bioprosthetic device 210 is shown to include four tissue layers, it is within the scope of the disclosure to include bioprosthetic device 210 having any number of tissue layers. As shown in FIG. 4, first row 226 is positioned to lie between top tissue layer 216 and one of the two middle tissue layers 215 positioned to lie adjacent to top tissue layer 216. Second row 227 is positioned to lie between the other middle tissue layer 215 and bottom tissue layer 218. It is within the scope of this disclosure, however, to include rows 226, 227 positioned to lie between any tissue layer of device 210.

Figure 6:
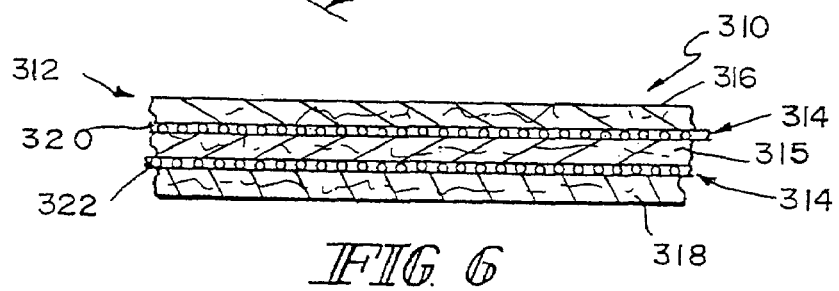
FIG. 6 is a sectional view of the bioprosthetic device of FIG. 5 showing first and second mesh members "sandwiched" between the tissue layers of the SIS portion of the device.

Yet another bioprosthetic device 310 is shown in FIGS. 5 and 6. Bioprosthetic device 310 is similar to devices, 10, 110, and 210 and includes an SIS portion 312 having a top tissue layer 316, a bottom tissue layer 318, and a middle tissue layer 315 positioned to lie between top and bottom tissue layers 316, 318. Top, bottom, and middle tissue layers 316, 318, 315 each include one or more layers of SIS tissue. Bioprosthetic device 310 further includes a synthetic portion 314 including first mesh member 320 and second mesh member 322. It is within the scope of this disclosure to include any type of synthetic mesh member. For example, bioabsorbable and/or non-bioabsorbable mesh members 320, 322 made of either woven or nonwoven PGA and/or PLA mixtures are included within the scope of disclosure of this invention. First mesh member 320 is coupled to and positioned to lie between top tissue layer 316 and middle tissue layer 315 and second mesh member 322 is coupled to and positioned to lie between middle tissue layer 315 and bottom tissue layer 318, as shown in FIGS. 5 and 6. Each of the first and second mesh members 320, 322 has a length, L, and a width, W, approximately equal to length, L, and width, W, of tissue layers 315, 316, 318, of SIS portion 312. It is understood that in some embodiments, it may be preferable for the mesh to be slightly smaller than the SIS portion.

In FIG. 5, second mesh member 322 is shown partially coated in comminuted SIS 340. Comminuted SIS may be used to fill the interstices of second mesh member 322 to provide a stronger device. Other means for reinforcing bioprosthetic device 10 may be employed, including suturing or tacking the various layers together. Further, while comminuted SIS is discussed with respect to the embodiment shown in FIG. 5, it is understood that comminuted SIS may be used to coat the mesh or fibers for any embodiment.

Figure 7:
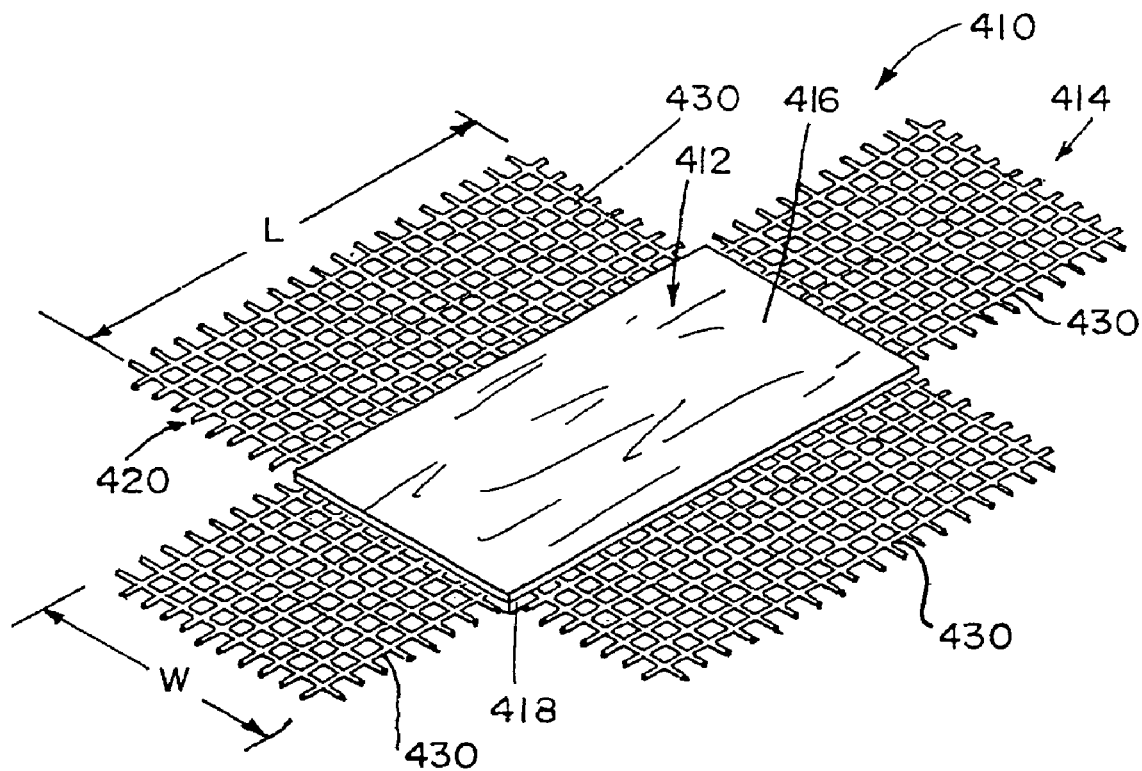
FIG. 7 is a perspective view showing an SIS portion of another bioprosthetic device being formed to include a top and a bottom tissue layer and further showing a synthetic portion being formed to include a mesh member having a body portion positioned to lie between the top and bottom tissue layers and outer wing portions provided for anchoring the device to surrounding soft tissue.

Another embodiment of the present invention includes a bioprosthetic device 410 having a synthetic portion 414 including a mesh member 420, as shown in FIG. 7. Similar to the previously mentioned devices, bioprosthetic device 410 includes an SIS portion 412 having a top tissue layer 416 and a bottom tissue layer 418 coupled to top tissue layer 416. Top and bottom tissue layers 416, 418 each include one or more layers of SIS tissue. Mesh member 420 includes a central body portion (not shown) and outer wing portions 430, as shown in FIG. 7. Outer wing portions 430 are extensions of the central body portion. Although four outer wing portions 430 are shown in FIG. 7, it is within the scope of this disclosure to include a mesh member having a body portion and any number of wing portions 430 coupled to the body portion. The central body portion of mesh member 420 is formed to include a length and a width equal to length, L, and width, W, of SIS portion 412. The central body portion is coupled to and positioned to lie between top tissue layer 416 and bottom tissue layer 418 of SIS portion 420. Each wing portion 430 is coupled to the central body portion of mesh member 420 and is positioned to extend beyond the length, L, and width, W, of SIS portion 412, as shown in FIG. 7. As mentioned before, outer wing portions 430 are extensions of the central body portion. Wing portions 430 provide additional material for anchoring bioprosthetic device 410 to the surrounding soft tissue. Because outer wing portions 430 extend beyond central body portion of mesh member 420, mesh member 420 has a length and a width greater than length, L, and width, W, of SIS portion 412.

Figure 8:
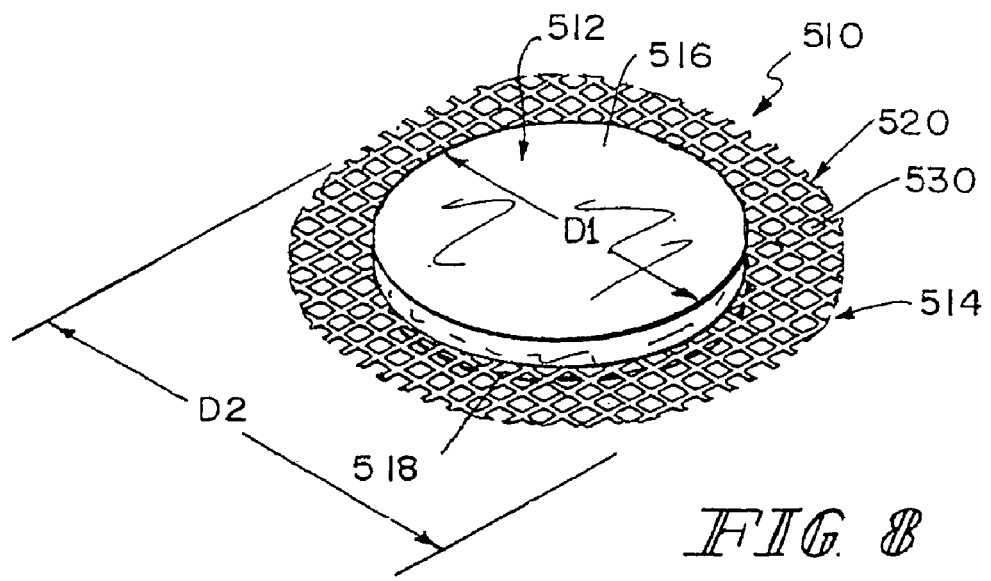
FIG. 8 is a perspective view showing an SIS portion of yet another bioprosthetic device being formed to include a circularly shaped top and bottom tissue layers each having a diameter, D1, and further showing a synthetic portion of the device being formed to include a circular mesh member positioned to lie between the top and bottom tissue layers and having a diameter, D2, which is larger than D1 so that an outer rim portion of the mesh member is formed to extend beyond the top and bottom tissue layers for anchoring the bioprosthetic device to the host tissue during surgery.

Yet another embodiment of the present invention is shown in FIG. 8 showing a bioprosthetic device 510 similar to bioprosthetic device 410, described above. Bioprosthetic device 510 includes an SIS portion 512 and a synthetic portion 514 coupled to SIS portion 512. SIS portion 512 includes a top tissue layer 516 which is circular in shape and a bottom tissue layer 518 which is also circular in shape. Each of the top and bottom tissue layers 516, 518 include one or more layers of SIS tissue. Top and bottom tissue layers 516, 518 each have a diameter, D1. The synthetic portion 514 of bioprosthetic device 510 includes a mesh member 520 coupled to and positioned to lie between top and bottom tissue layers 516, 518. Mesh member 520 is circular in shape and has a diameter, D2, which is greater than diameter, D1, of synthetic portion 512. Therefore, as shown in FIG. 8, an outer rim portion 530 of mesh member 520 is provided. Similar to outer wing portions 430 of bioprosthetic device 410, shown in FIG. 7, outer rim portion 530 of bioprosthetic device 510 provides additional material for anchoring bioprosthetic device 510 to the surrounding soft tissue during surgery.

Figure 9:
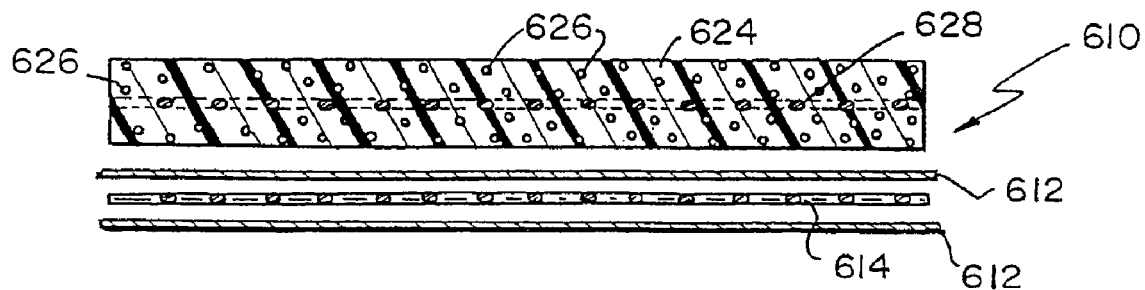
FIG. 9 is a sectional view of a bioprosthetic device similar to the bioprosthetic device of FIG. 5, having two SIS layers, a reinforcing mesh material between the SIS layers, and a reinforced three-dimensional foam portion adjacent one of the SIS layers.

FIG. 9 shows a three-dimensional prosthetic device 610, having several SIS layers 612, a synthetic reinforcing material 614 positioned to lie between the SIS layers 612, and a three-dimensional synthetic portion 624. The SIS layer 612 may comprise any number of tissue layers. Furthermore, illustratively, if more than one layer is used, the layers may be laminated together. It is included within the scope of this disclosure to provide perforated tissue layers or any other physical configuration of SIS. As with the embodiments shown in FIGS. 5-8, any number of SIS and reinforcing layers may be used, depending on the application.

Synthetic reinforcing material 614 illustratively comprises a two-dimensional fibrous matrix construct, as shown in FIGS. 5-8, and may have the same length and width as the SIS layer, as shown in FIG. 5, may be slightly smaller, or may extend beyond the ends of the SIS layer, as shown in FIGS. 7-8. Alternatively, synthetic reinforcing material may comprise a three-dimensional mesh, textile, felt, or other fibrous nonwoven construct, which may be shaped or formed for the particular application. The fibers comprise any biocompatible material, including PLA, PGA, PCL, PDO, TMC, PVA, or copolymers or blends thereof. In one example, mesh material is a 95:5 copolymer of PLA/PGA.

Three-dimensional synthetic portion 624 is a nonwoven material prepared to have numerous interconnecting pores or voids 626. Illustratively, the size of the voids may range from 20 to 400 microns. However, the size of the voids may be adjusted depending on the application, and the size may be manipulated by changing process steps during construction by altering freezing temperature, rate of temperature change and vacuum profile. Examples of various polymers that may be used for the foam, as well as various lyophilization profiles to control porosity, are described in U.S. Pat. Nos. 6,333,029 and 6,355,699, hereby incorporated by reference. Optionally, three-dimensional synthetic portion 624 further comprises a synthetic reinforcing layer 628 embedded within the foam. Reinforcing layer 628 illustratively provides enhanced mechanical integrity to the three-dimensional synthetic portion. In an illustrated embodiment, a Vicryl knitted mesh is used. However, other reinforcing layers may be used.

Optionally, three-dimensional synthetic portion 624 may be a hybrid ECM/synthetic foam portion. In making such a foam, the polymer solution is mixed with a slurry of comminuted SIS prior to lyophilization. See U.S. Application No. 60/388,761 entitled "Extracellular Matrix Scaffold and Method for Making the Same", hereby incorporated by reference.

Figure 10:
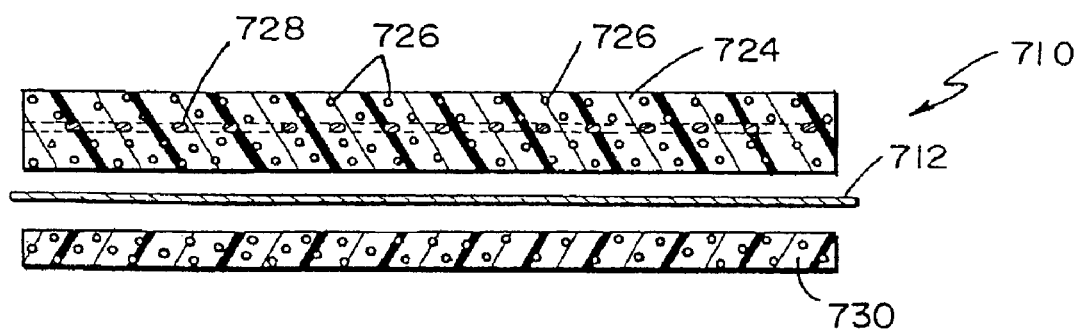
FIG. 10 is sectional view of another bioprosthetic device, wherein the SIS layer is sandwiched between two foam layers.
Figure 11:
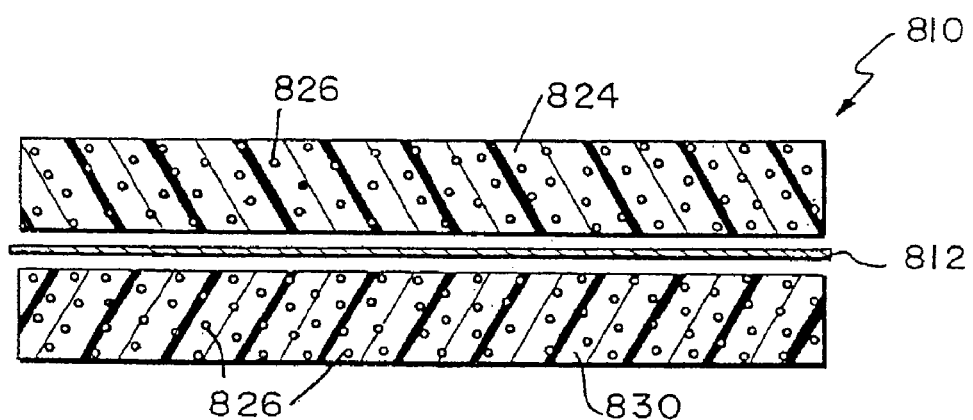
FIG. 11 is sectional view of another bioprosthetic device, wherein a foam layer is sandwiched between SIS layers.

FIG. 10 shows a bioprosthetic device 710 that is similar to that of FIG. 9. In FIG. 10, the SIS layer 712 is sandwiched between two three-dimensional synthetic portions 724, 730. Illustratively, both three-dimensional synthetic portions are foams, having voids 726. As shown, three-dimensional synthetic portion 724 has a reinforcing mesh 728, while three-dimensional synthetic portion 730 does not have a reinforcing member. However, other arrangements are possible, and FIG. 11 shows an embodiment 810 where the SIS layer 812 is sandwiched between two three-dimensional synthetic portions 824, 830, neither of which has reinforcing members.

Figure 12:
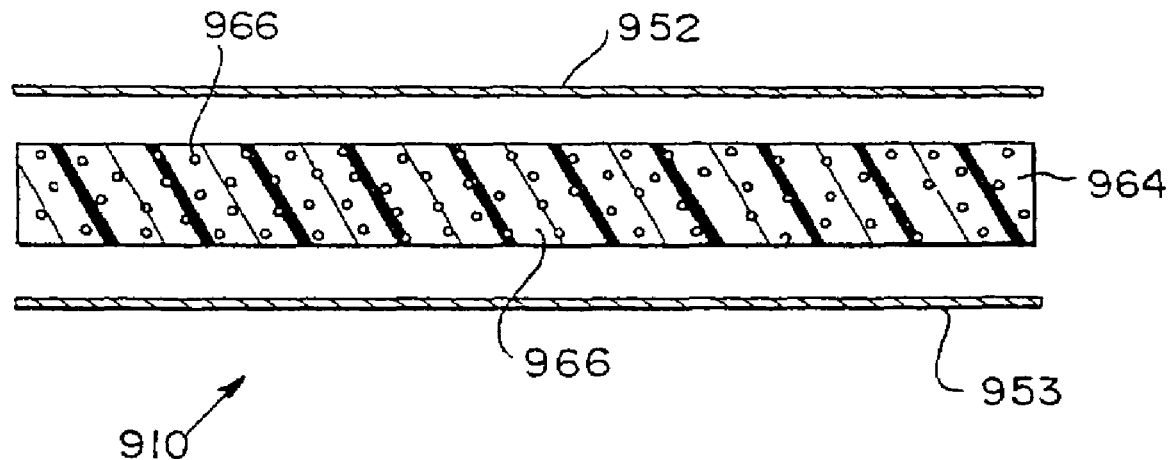
FIG. 12 is a sectional view of another bioprosthetic device, wherein a three-dimensional synthetic layer is sandwiched between two SIS layers.

FIG. 12 shows another embodiment 910, wherein a single three-dimensional synthetic portion 964 is sandwiched between two SIS layers 952, 953. As shown, three-dimensional synthetic portion 964 is a foam, with voids 966, but other three-dimensional synthetic portions may be used.

Figure 13:
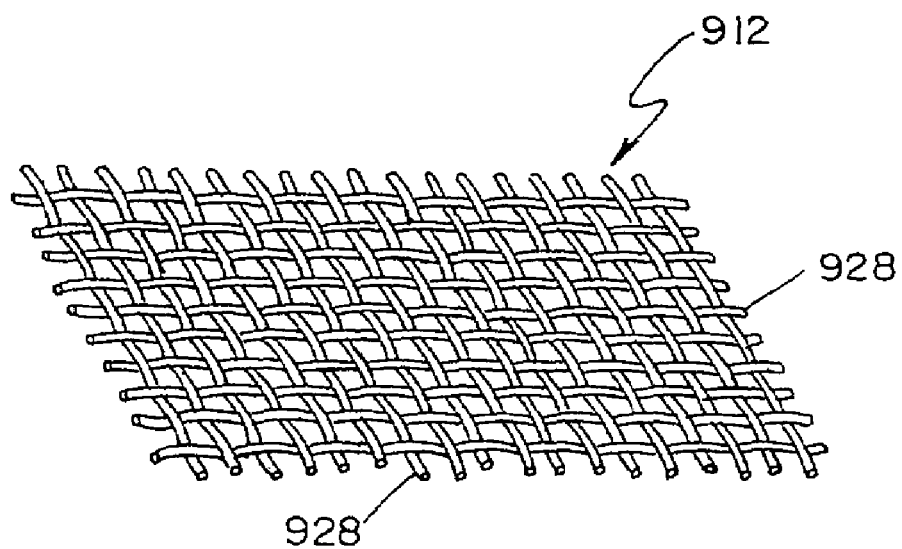
FIG. 13 is a perspective view showing an SIS portion for use in another bioprosthetic device, wherein the SIS layer is made from weaving strips of SIS.

FIG. 13 shows a woven mesh 912 made from strips 928 of SIS. Fresh, lyophilized, or laminated strips of SIS may be cut into narrower strips and woven into a mesh. The strips may be of any width, depending on the application, for example 0.1 to 20 mm, more particularly 1.0 mm wide strips. Optionally, the woven strips may be laminated together to provide enhanced mechanical support. The SIS woven mesh may be used as the SIS layer in any of the above embodiments. When used with the synthetic foams, if sufficient space is provided in the weaving, the foams will form through the spaces within the mesh.

Reinforced SIS devices may also be fabricated using other processes. For example, a synthetic polymer mesh coated with comminuted SIS (or other ECM) may be sandwiched in the middle of twenty strips of SIS (10 layers on each side), laminated under high pressure, and subsequently dried under vacuum pressure in a flat-bed gel drier system. The comminuted SIS (or other comminuted ECM) may be prepared in the manner described in U.S. patent application Publication No. 20030044444 A1 entitled "Porous Extracellular Matrix Scaffold and Method" by P. Malaviya et al., the entirety of which is hereby incorporated by reference.

Such a laminated and dried implant is significantly more resistant to delamination (175 minutes to delaminate using a water bath delamination protocol described below) as compared to implants made either with high pressure lamination but without the comminuted SIS coating (60 minutes to delaminate) or with the comminuted SIS coating but without the high pressure lamination (20-30 minutes to delaminate). It is believed that coating the synthetic mesh with comminuted SIS and then initiating lamination under high pressure has a synergistic effect on the resistance to delamination.

Such relatively high, positive pressure may be applied in a number of different manners. In an exemplary implementation, the relatively high, positive pressure is applied by use of a pneumatic cylinder press assembly. Other positive pressure sources may also be used. Moreover, the pressure may be applied in a wide range of magnitudes.

Implants fabricated in such a manner may have higher, and perhaps significantly higher, mechanical properties. In specific exemplary uses, such implants may be used where diseased/damaged tissue needs to be regenerated under high load conditions. For example, such implants may be used for the augmentation of damaged/resected hip capsule following primary or revision hip surgery, for patellar tendon regeneration, for the repair of large rotator cuff tears, for spinal ligament regeneration, and the like.

Other methods for fabricating reinforced SIS implants are also contemplated. For example, the surface of the synthetic polymer is characteristically hydrophobic in nature, while the SIS surface is hydrophilic. The surface of the synthetic polymer component may be modified to render it more hydrophilic, and, as a result, more compatible with the SIS surface. The more hydrophilic polymer surface creates a like-like attraction (e.g., weak force and hydrogen bonding) between the synthetic polymer component and the SIS thereby reducing the occurrences of delamination of the device. Such modification of the surface of the polymer component may also be used in conjunction with concepts described above for fabricating a pressure-laminated and vacuum-dehydrated composite.

Surface modification of the synthetic polymer component, such as a resorbable polyester, may be accomplished by numerous techniques such as, for example, traditional wet chemistry or gas plasma processing. Traditional chemistries may include surface hydrolysis and amidation techniques. Base or acid catalyzed hydrolysis of the synthetic polymer (e.g., polyester) creates pendant hydroxyl and carboxylic acid moieties, while treatment with a bifunctional amine affords free amine functionalities coupled to the surface. It should be appreciated that such a bifunctional amine may have an amine on both ends thereof, or, alternatively, may have an amine on one end with any type of hydrophilic group on the other end.

Gas plasma treatment of the synthetic polymer generates high energy reactive species that bond to surfaces. For example, treatment of a polymer surface with ammonia plasma generates an amine functionalized surface. Similarly, an oxidative plasma may be produced by filtering aqueous hydrogen peroxide into the plasma chamber at approximately 400 mTorr and applying an approximately 200 Watt radio frequency for approximately 3, 5, or 10 minutes.

It should be appreciated that such treatment of the synthetic polymer may also be used to functionalize non-absorbable polymers.

By taking these approaches to strengthen SIS laminates, crosslinking of the SIS material may be avoided, thus retaining more of its biochemical and biological properties. However, to fit the needs of a given implant design, crosslinking of the SIS material may be used in conjunction with the herein described strengthening techniques.

The composite implants described herein may be used where diseased or damaged tissue needs to be regenerated under high load conditions, for example, for the augmentation of damaged/resected hip capsule following primary or revision hip surgery, for patellar or Achilles tendon regeneration, for the repair of large rotator cuff tears, for spinal ligament regeneration, etcetera.

It should be appreciated that devices may be fabricated which include a combination of both surface treatment and coating of the synthetic polymer component. For example, the synthetic polymer component may first be treated to enhance the hydrophilicity of it surface (e.g., by use of wet chemistry or gas plasma treatment). Once treated, the synthetic polymer component may be coated in comminuted SIS (or other naturally occurring extracellular matrix material) in the manner described above. Thereafter, the synthetic polymer component may be secured to layers of SIS (or other ECM). For example, the treated and coated synthetic polymer layer may be laminated to one or more SIS layers under high pressure and subsequently dried under vacuum pressure in the manner described above.

While the devices shown in FIGS. 9-13 specific embodiments, it is understood that other arrangements are within the scope of this invention. For example, in FIGS. 10-11, an SIS layer is sandwiched between two three-dimensional foam sections, with or without a reinforcing material embedded within the foam. Additional reinforcing layers, as shown in FIG. 9 may be used with these embodiments. Similarly, when a single three-dimensional foam portion is sandwiched between two SIS layers, as in FIG. 12, a layer of reinforcing material may be used, depending upon the application. In still another embodiment, the reinforcing portion may comprise a three-dimensional mesh or textile, and the three-dimensional foam portion may be omitted. It is also within the scope of this disclosure to further define the SIS portion to include sheets, perforated sheets, or any other physical configuration of SIS. Furthermore, the synthetic portion may comprise Prolene™ (Ethicon, Inc, Somerville, N.J.) meshes and/or sutures, Vicryl™ (Ethicon, Inc, Somerville, N.J.) meshes and/or sutures, Mersilene™ (Ethicon, Inc, Somerville, N.J.) meshes, PDS II™ (Ethicon, Inc., Somerville, N.J.) meshes or sutures, Panacryl™ (Ethicon, Inc., Somerville, N.J.) meshes or sutures, and Monocryl™ meshes or sutures, for example. Additional two or three-dimensional meshes may be constructed for particular applications. Further it is within the scope of this disclosure to include bioprosthetic devices where the SIS portion includes any number of tissue layers and where multiple tissue layers are positioned to lie along each synthetic layer. The SIS layers may be dehydrated prior to or subsequent to assembly of the device. Further, any shape and/or orientation of the SIS portion and the synthetic portion of the bioprosthetic device is within the scope of this disclosure; FIGS. 1-13 are merely examples of various embodiments of the present invention.

EXAMPLE 1

Sheets of clean, disinfected porcine SIS material were obtained as described in U.S. Pat. Nos. 4,902,508 and 4,956,178. Ten strips, 3.5 inches wide and 6 inches long were cut. The strips were hydrated by placing in RO water, at room temperature, for 5 minutes.

To assemble the implant, five SIS strips were placed on top of each other, while ensuring no air bubbles were trapped between the strips. A knitted Panacryl™ mesh, 2 inches wide and 5 inches long, was placed centrally on the 5-layer thick SIS strip. The mesh had been pretreated to remove any traces of oil or other contaminants due to handling. This was done by a series of rinses, each 2 minutes long, in 100%, 90%, 80%, 70% ethanol (200 proof) in RO water, followed by a final 5 minute in RO water. Subsequently, a second 5-layer thick strip of SIS was assembled and placed to sandwich the mesh between the two SIS strips.

The implant was dried under vacuum pressure using a gel drier system (Model FB-GD-45, Fisher Scientific, Pittsburgh, Pa.) for 3 hours. The gel drier bed temperature was set at 30° C. for the procedure. This drying procedure results in "squeezing out" of the bulk water in the implant and also reduces the amount of bound water within the tissue, resulting in a final moisture of between 7%-8%. This process also results in a physical crosslinking between the laminates of SIS and between the mesh and adjacent SIS laminates.

Non-reinforced SIS strips were made in the same way as described, except that no mesh material was placed between the strips of SIS.

EXAMPLE 2

This example describes the preparation of three-dimensional composite tissue implants incorporating a biodegradable SIS laminated sheet, a synthetic reinforcement in the form of a biodegradable mesh, and a synthetic degradable foam.

A solution of the polymer to be lyophilized to form the foam component was prepared in a four step process. A 95:5 weight ratio solution of 1,4-dioxane/(40/60 PCL/PLA) was made and poured into a flask. The flask was placed in a water bath, stirring at 60-70° C. for 5 hrs. The solution was filtered using an extraction thimble, extra coarse porosity, type ASTM 170-220 (EC) and stored in flasks.

A three-dimensional mesh material composed of a 95:5 copolymer of polylactic/polyglycolic acid (PLA/PGA) knitted mesh was rendered flat to control curling by using a compression molder at 80° C. for 2 min. After preparing the mesh, 0.8-mm metal shims were placed at each end of a 4×4 inch aluminum mold, and the mesh was sized to fit the mold. The synthetic mesh was then laid into the mold, covering both shims. Next, an SIS laminated sheet was placed over the mesh followed by additional shims to cover the edges of the SIS and synthetic mesh.

The polymer solution (40:60 PCL/PLA) was added into mold such that the solution covered the sheet of SIS as well as the mesh and reached a level of 3.0 mm in the mold.

The mold assembly then was placed on the shelf of the lyophilizer (Virtis, Gardiner, N.Y.) and the freeze dry sequence begun. The freeze dry sequence used in this example was: 1) −17° C. for 60 minutes; 2) −5° C. for 60 minutes under vacuum of 100 mT; 3) 5° C. for 60 minutes under vacuum of 20 mT; 4) 20° C. for 60 minutes under vacuum of 20 mT.

After the cycle was completed, the mold assembly was taken out of the freeze drier and allowed to degas in a vacuum hood for 2 to 3 hours, and stored under nitrogen.

The resultant bioprosthetic device has a structure as illustrated in FIG. 9. The three-dimensional mesh provides both mechanical strength and three-dimensional structure to the resultant device. The foam may be shaped or sculpted for the particular application, and the mesh/SIS layers may be trimmed to fit. It is also understood that the mold could be provided in the desired shape, reducing or obviating the need for sculpting or trimming.

EXAMPLE 3

This example uses the process outlined in Example 2 to fabricate a biodegradable composite scaffold of the present invention where the foam component is a 65:35 PGA/PCL copolymer.

EXAMPLE 4

This example uses the process outlined in Example 2 to fabricate a biodegradable composite scaffold of the present invention where the synthetic knitted mesh component is composed of 100% PDO.

EXAMPLE 5

This example uses the process outlined in Example 2 to fabricate a biodegradable composite scaffold of the present invention where in place of a three-dimensional mesh, the synthetic component is a nonwoven fibrous structure composed of either 100% PDO, 100% 90/10 PGA/PLA or a combination of the two.

EXAMPLE 6

This example uses the process outlined in Example 2 to fabricate a biodegradable composite scaffold of the present invention where the SIS component is soaked overnight in the polymer solution (5% wt 60/40 PLA/PCL in dioxane) prior to placement over the synthetic mesh. Enhanced lamination between the components was found when this additional soaking step was added to the process as evidenced by a composite with a greater degree of handlability.

EXAMPLE 7

This example uses the process outlined in Example 2 to fabricate a biodegradable composite scaffold of the present invention where the SIS component is a single layer sheet rather than a laminated sheet.

EXAMPLE 8

This example uses the process outlined in Example 2 to fabricate a biodegradable composite scaffold of the present invention where the SIS laminated sheet is perforated with holes ranging from 1 mm-1 cm. These perforations allow for enhanced penetration of the polymer solution through the SIS sheet.

EXAMPLE 9

This example uses the process outlined in Example 2 to fabricate a biodegradable composite scaffold of the present invention where the SIS reinforcing component is a "woven mesh" of laminated strips sandwiched between two layers of 60/40 PLA/PCL foam. FIG. 13 shows such a woven mesh. FIG. 11, wherein the SIS layer is a woven mesh of FIG. 13, illustrates the construct of this Example.

EXAMPLE 10

A soaking test was performed to test resistance to delamination. Implants made as specified in Example 1 (both reinforced and non-reinforced) were cut into several strips 1 cm wide by 5 cm long, using a #10 scalpel blade. The strips were immersed in RO water, at room temperature for 1, 2, 5, 10, 20, 30, or 60 minutes. Delamination was detected at the edges of the implants by direct visual observation. All implants showed obvious signs of delamination at 1 hour. In non-reinforced implants, delamination was first visually observed between 40-60 minutes, whereas in the reinforced samples delamination was apparent between 20-30 minutes.

EXAMPLE 11

This example illustrates the enhanced mechanical properties of a construct reinforced with absorbable mesh. Preparation of three-dimensional elastomeric tissue implants with and without a reinforcement in the form of a biodegradable mesh are described. While a foam is used for the elastomeric tissue in this example, it is expected that similar results will be achieved with an ECM and a biodegradable mesh.

A solution of the polymer to be lyophilized to form the foam component was prepared in a four step process. A 95/5 weight ratio solution of 1,4-dioxane/(40/60 PCL/PLA) was made and poured into a flask. The flask was placed in a water bath, stirring at 70° C. for 5 hrs. The solution was filtered using an extraction thimble, extra coarse porosity, type ASTM 170-220 (EC) and stored in flasks.

Reinforcing mesh materials formed of a 90/10 copolymer of polyglycolic/polylactic acid (PGA/PLA) knitted (Code VKM-M) and woven (Code VWM-M), both sold under the tradename VICRYL were rendered flat by ironing, using a compression molder at 80° C./2 min. After preparing the meshes, 0.8-mm shims were placed at each end of a 15.3× 15.3 cm aluminum mold, and the mesh was sized (14.2 mm) to fit the mold. The mesh was then laid into the mold, covering both shims. A clamping block was then placed on the top of the mesh and the shim such that the block was clamped properly to ensure that the mesh had a uniform height in the mold. Another clamping block was then placed at the other end, slightly stretching the mesh to keep it even and flat.

As the polymer solution was added to the mold, the mold was tilted to about a 5 degree angle so that one of the non-clamping sides was higher than the other. Approximately 60 ml of the polymer solution was slowly transferred into the mold, ensuring that the solution was well dispersed in the mold. The mold was then placed on a shelf in a Virtis (Gardiner, N.Y.), Freeze Mobile G freeze dryer. The following freeze drying sequence was used: 1) 20° C. for 15 minutes; 2) −5° C. for 120 minutes; 3) −5° C. for 90 minutes under vacuum 100 milliTorr; 4) 5° C. for 90 minutes under vacuum 100 milliTorr; 5) 20° C. for 90 minutes under vacuum 100 milliTorr. The mold assembly was then removed from the freezer and placed in a nitrogen box overnight. Following the completion of this process the resulting implant was carefully peeled out of the mold in the form of a foam/mesh sheet.

Nonreinforced foams were also fabricated. To obtain nonreinforced foams, however, the steps regarding the insertion of the mesh into the mold were not performed. The lyophilization steps above were followed.

EXAMPLE 12

Lyophilized 40/60 polycaprolactone/polylactic acid, (PCL/PLA) foam, as well as the same foam reinforced with an embedded VICRYL knitted mesh, were fabricated as described in Example 3. These reinforced implants were tested for suture pull-out strength and compared to non-reinforced foam prepared following the procedure of Example 11.

For the suture pull-out strength test, the dimensions of the specimens were approximately 5 cm×9 cm. Specimens were tested for pull-out strength in the wale direction of the mesh (knitting machine axis). A size 0 polypropylene monofilament suture (Code 8834H), sold under the tradename PROLENE (by Ethicon, Inc., Somerville, N.J.) was passed through the mesh 6.25 mm from the edge of the specimens. The ends of the suture were clamped into the upper jaw and the mesh or the reinforced foam was clamped into the lower jaw of an Instron model 4501 (Canton, Mass.). The Instron machine, with a 20 lb load cell, was activated using a crosshead speed of 2.54 cm per minute. The ends of the suture were pulled at a constant rate until failure occurred. The peak load (lbs.) experienced during the pulling was recorded.

The results of this test are shown below in Table 1.

TABLE 1

Suture Pull-Out Data (lbs.)

| Time | Foam | Mesh | Foamed Mesh |
|---|---|---|---|
| 0 Day | 0.46 | 5.3 +/− 0.8 | 5.7 +/− 0.3 |
| 7 Day* | — | 4.0 +/− 1.0 | 5.0 +/− 0.5 |

*exposed for 7 days to phosphate buffered saline at 37° C. in a temperature controlled water bath.

These data show that a reinforced foam has improved pull-out strength verses either foam or mesh alone.

EXAMPLE 13

Sheets of clean, disinfected porcine SIS material were obtained as described in patents U.S. Pat. Nos. 4,902,508 and 4,956,178. Twenty strips, 3.5 inches wide and 6 inches long were cut. The strips were hydrated by placing in RO water, at room temperature, for 5 minutes.

To assemble the implant, ten SIS strips were placed longitudinally on top of each other, while ensuring no air bubbles were trapped between the strips. A knitted Panacryl™ mesh, 2 inches wide and 5 inches long, was immersed in a comminuted SIS suspension (disclosed in U.S. patent publication 2003004444 A1) (approximately 1% solids w/v). This results in a near-uniform coating of the synthetic mesh with the wet fibers of the SIS suspension such that the SIS fibers are intertwined and interlocked with the porous knitted mesh. The coated mesh was placed centrally on the 10-layer thick SIS strip. Subsequently, a second 10-layer thick strip of SIS was assembled and placed to sandwich the coated mesh between the two SIS strips.

Lamination of the thus assembled implant was initiated under high pressure using a pneumatic cylinder press (Model BTP-501-A, TRD Manufacturing Inc., Loves Park, Ill. 61111.) The press was operated at 40 psi air pressure to drive the piston, which resulted in a total compressive force of approximately 4000 lbs on the assembled implant. This force created an approximate average lamination pressure of 180 psi on the implant. The sample was compressed for 15 minutes at room temperature. This process resulted in a "squeezing out" of most of the bulk water associated with the SIS laminates and comminuted SIS and created a partially wet laminated implant.

The implant was subsequently dried under vacuum pressure using a flat-bed gel drier system (Model FB-GD-45, Fisher Scientific, Pittsburgh, Pa.) for 3 hours. The gel drier bed temperature was set at 30° C. for the procedure. This drying procedure resulted in a further reduction of the bulk water associated with the implant and also reduced the amount of bound water within the implant, resulting in a final moisture content between 7%-8%. This process also results in a physical crosslinking between the laminates of SIS and the comminuted SIS coating the synthetic mesh by further increasing the surface contact area of SIS material.

Implants were also made as described above but without coating the Panacryl™ mesh with the comminuted SIS fibers.

EXAMPLE 14

An agitation test was performed to test for resistance to delamination. High-pressure laminated implants made as described in Example 13 (both with and without SIS coating on the mesh) were cut into several strips 1 cm wide and 5 cm long. Each strip was placed in 20 mL of reverse osmosis water at room temperature in a 50 mL glass flask. The flasks were secured on a shaker table set to agitate the samples at 300 rpm. Every five minutes the strips were examined for delamination between the SIS laminates and the synthetic mesh. On average, reinforced implants without the comminuted SIS-coated mesh delaminated after 60 minutes of agitation, whereas, reinforced implants with the comminuted SIS-coating delaminated after 175 minutes.

It is expected that high pressure laminated SIS implants reinforced with a comminuted SIS coated synthetic mesh will also have higher (and perhaps significantly higher) mechanical properties (e.g. higher ball burst strength) as compared with implants made without high pressure lamination or without a comminuted SIS coating on the synthetic mesh.

Although the invention has been described in detail with reference to certain preferred embodiments, variations and modifications exist within the scope and spirit of the invention as described and defined in the following claims.

The invention claimed is:

1. A method of making a bioprosthetic device, the method comprising the steps of:
   coating a synthetic layer with a comminuted naturally occurring extracellular matrix material;
   positioning the coated synthetic layer between a first layer of naturally occurring extracellular matrix material and a second layer of naturally occurring extracellular matrix material to make an assembly; and
   applying positive pressure to the assembly to initiate lamination of the first and second layers of naturally occurring extracellular matrix material to the coated synthetic layer.

2. A method of making a bioprosthetic device, the method comprising the steps of:
   coating a synthetic layer with comminuted naturally occurring extracellular matrix material;

positioning the coated synthetic layer between a first layer of naturally occurring extracellular matrix material and a second layer of naturally occurring extracellular matrix material to make an assembly; and operating a press to exert positive pressure on the assembly to initiate lamination of the first and second layers of naturally occurring extracellular matrix material to the coated synthetic layer.

3. The method of claim 1, wherein the applying step comprises pressing the assembly together.

4. The method of claim 1, wherein the applying step comprises pressing the assembly with a pneumatic press.

5. The method of claim 1, wherein the applying step comprises:

positioning the assembly in a press, and operating the press to exert pressure on assembly.

6. The method of claim 1, further comprising the step of drying the assembly after the applying step.

7. The method of claim 1, wherein both the first and second naturally occurring extracellular matrix material layers comprise a small intestine submucosa (SIS) layer.

8. The method of claim 1, wherein the synthetic layer comprises a fibrous material.

9. The method of claim 1, wherein the coating step comprises immersing the synthetic layer in a suspension of comminuted naturally occurring extracellular matrix material.

10. The method of claim 1, wherein the applying step comprises applying a compressive force that creates an average lamination pressure of approximately 180 psi on the assembly.

11. The method of claim 6, wherein the drying step comprises drying the assembly under vacuum pressure.

12. The method of claim 7, wherein the SIS layer comprises a plurality of SIS strips laminated together.

13. The method of claim 7, wherein the SIS layer comprises a woven mesh of strips of SIS.

14. The method of claim 8, wherein the fibrous material is selected from the group consisting of mesh, textile, and felt.

15. The method of claim 8, wherein the fibrous material is a bioabsorbable material selected from the group consisting of polylactic acid (PLA), polyglycolic acid (PGA), polycaprolactone (PCL), polydioxanone (PDO), trimethylene carbonate (TMC), polyvinyl alcohol (PVA), copolyiners thereof, and blends thereof.

16. The method of claim 2, wherein the operating step comprises operating a pneumatic press to exert positive pressure on the assembly.

17. The method of claim 2, further comprising the step of drying the assembly after the operating step.

18. The method of claim 2, wherein both the first and second naturally occurring extracellular matrix material layers comprise an SIS layer.

19. The method of claim 2, wherein the SIS layer comprises a woven mesh of strips of SIS.

20. The method of claim 2, wherein the synthetic layer comprises a fibrous material.

21. The method of claim 2, wherein the operating step comprises operating the press to exert a compressive force that creates an average lamination pressure of approximately 180 psi on the assembly.

22. The method of 17, wherein the drying step comprises drying the assembly under vacuum pressure.

23. The method of claim 18, wherein the SIS layer comprises a plurality of SIS strips laminated together.

24. The method of claim 20, wherein the fibrous material is selected from the group consisting of mesh, textile, and felt.

25. The method of claim 20, wherein the fibrous material is a bioabsorbable material selected from the group consisting of PLA, PGA, PCL, PDO, TMC, PVA, copolyiners thereof, and blends thereof.

* * * * *

UNITED STATES PATENT AND TRADEMARK OFFICE
CERTIFICATE OF CORRECTION

PATENT NO. : 7,569,233 B2  Page 1 of 1
APPLICATION NO. : 11/110169
DATED : August 4, 2009
INVENTOR(S) : Malaviya et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 434 days.

Signed and Sealed this

Seventh Day of September, 2010

David J. Kappos
*Director of the United States Patent and Trademark Office*